(12) United States Patent
Watanabe et al.

(10) Patent No.: US 12,265,054 B2
(45) Date of Patent: Apr. 1, 2025

(54) SENSOR ELEMENT AND GAS DETECTION METHOD USING SENSOR ELEMENT

(71) Applicant: NGK INSULATORS, LTD., Nagoya (JP)

(72) Inventors: Yusuke Watanabe, Nagoya (JP); Takayuki Sekiya, Nisshin (JP)

(73) Assignee: NGK INSULATORS, LTD., Nagoya (JP)

( * ) Notice: Subject to any disclaimer, the term of this patent is extended or adjusted under 35 U.S.C. 154(b) by 191 days.

(21) Appl. No.: 17/702,005

(22) Filed: Mar. 23, 2022

(65) Prior Publication Data

US 2022/0308010 A1  Sep. 29, 2022

(30) Foreign Application Priority Data

Mar. 29, 2021 (JP) .................................. 2021-055733
Feb. 18, 2022 (JP) .................................. 2022-024171

(51) Int. Cl.
*G01N 27/41* (2006.01)
*G01N 27/407* (2006.01)
(Continued)

(52) U.S. Cl.
CPC ......... *G01N 27/41* (2013.01); *G01N 27/4071* (2013.01); *G01N 27/4075* (2013.01); *G01N 27/409* (2013.01); *G01N 33/0037* (2013.01)

(58) Field of Classification Search
CPC ............... G01N 27/41; G01N 27/4071; G01N 27/4075; G01N 27/409; G01N 27/417; G01N 33/0037
See application file for complete search history.

(56) References Cited

U.S. PATENT DOCUMENTS 5,763,763 A   6/1998  Kato et al.
5,893,968 A * 4/1999  Kato ..................... G01N 27/419
                                             73/23.31

(Continued)

FOREIGN PATENT DOCUMENTS

JP        8050781 B2     6/2000
JP     2014-190940 A    10/2014

(Continued)

OTHER PUBLICATIONS

Unexamined U.S. Appl. No. 17/702,014, filed Mar. 23, 2022.
Unexamined U.S. Appl. No. 17/702,018, filed Mar. 23, 2022.

*Primary Examiner* — Brian W Cohen
*Assistant Examiner* — Shizhi Qian
(74) *Attorney, Agent, or Firm* — MATTINGLY & MALUR, PC

(57) ABSTRACT

A sensor element includes a base part including a plurality of oxygen-ion-conductive solid electrolyte layers stacked; a measurement-object gas flow part for introduction and flow of a measurement-object gas through one end part in a longitudinal direction of the base part; a main pump cell including an inner main pump electrode disposed on an inner surface of the measurement-object gas flow part, and an outer pump electrode; a target-gas-decomposing pump cell including a target-gas-decomposing pump electrode disposed at a position farther from the one end part than the inner main pump electrode, and an outer pump electrode; a residual-oxygen-measuring pump cell including a residual-oxygen-measuring electrode disposed at a position farther from the one end part than the inner main pump electrode, and an outer pump electrode; and a reference electrode. The target-gas-decomposing pump electrode comprises a metal material that has catalytic activity of decomposing a target gas to be measured.

14 Claims, 7 Drawing Sheets

(51) Int. Cl.
*G01N 27/409* (2006.01)
*G01N 33/00* (2006.01)

(56) References Cited

U.S. PATENT DOCUMENTS

| | | | |
|---|---|---|---|
| 2001/0023823 A1* | 9/2001 | Takahashi | G01N 33/0037 |
| | | | 204/426 |
| 2004/0069629 A1* | 4/2004 | Tanaka | G01N 27/419 |
| | | | 204/426 |
| 2010/0243447 A1* | 9/2010 | Fujisaki | G01N 27/4075 |
| | | | 204/292 |
| 2011/0147214 A1 | 6/2011 | Fujita et al. | |
| 2019/0137441 A1* | 5/2019 | Nakagaki | G01N 27/4071 |
| 2020/0003725 A1* | 1/2020 | Nakagaki | G01N 27/4075 |
| 2020/0041442 A1* | 2/2020 | Watanabe | G01N 27/4072 |
| 2020/0064302 A1* | 2/2020 | Sekiya | G01N 27/4075 |
| 2020/0080459 A1* | 3/2020 | Okamoto | F02D 41/1463 |

FOREIGN PATENT DOCUMENTS

| | | |
|---|---|---|
| JP | 2014-209128 A | 11/2014 |
| JP | 6292735 B2 | 3/2018 |

\* cited by examiner

SENSOR ELEMENT AND GAS DETECTION METHOD USING SENSOR ELEMENT

CROSS-REFERENCE TO RELATED APPLICATION

The present application claims priority from Japanese applications JP2021-055733, filed on Mar. 29, 2021 and JP2022-024171, filed Feb. 18, 2022, the contents of which are hereby incorporated by reference into this application.

BACKGROUND OF THE INVENTION

Technical Field of the Invention

The present invention relates to a sensor element using an oxygen ion conductive solid electrolyte. The present invention also relates to a detection method of a target gas to be measured in a measurement-object gas using the sensor element.

Background Art

A gas sensor is used for detection or measurement of concentration of an objective gas component (oxygen $O_2$, nitrogen oxide NOx, ammonia $NH_3$, hydrocarbon HC, carbon dioxide $CO_2$, etc.) in a measurement-object gas, such as exhaust gas of automobile. For example, conventionally, the concentration of the objective gas component in exhaust gas of an automobile is measured, and an exhaust gas cleaning system mounted on the automobile is optimally controlled based on the measurement.

As such a gas sensor, a gas sensor equipped with a sensor element using an oxygen ion conductive solid electrolyte such as zirconia ($ZrO_2$) is known. The gas sensor detects an electromotive force or a current value corresponding to the concentration of an objective gas component in a measurement-object gas by using the oxygen ion conductivity of the solid electrolyte, thereby detecting the gas component and measuring the concentration.

For example, JP3050781B2 discloses a gas sensor that controls the oxygen partial pressure to such a low level that does not substantially affect measurement of the amount of a measurement-object gas component by means of a first electrochemical pumping cell and a second electrochemical pumping cell, and detects a current value corresponding to the oxygen generated by reduction or decomposition of the measurement-object gas component. In other words, oxygen is preliminarily removed by the first electrochemical pumping cell and the second electrochemical pumping cell, and the oxygen derived from the objective gas component (for example, nitrogen oxide NOx) is detected.

JP3050781B2 also indicates that the concentration of nitrogen oxide (NOx) and the detected current value have a linear relationship (FIG. 5).

JP2014-209128A and JP2014-190940A disclose a NOx sensor. In the disclosure, the NOx sensor has a main pump cell and an auxiliary pump cell for adjusting oxygen concentration, and as an inner pump electrode of the main pump cell, for example, a cermet electrode of Pt containing 1% Au and zirconia is used.

JP6292735B2 discloses a NOx sensor. In the disclosure, the NOx sensor has a pump cell for discharging oxygen ions from a measurement-object gas chamber, and a Pt—Au alloy is used for a pump electrode constituting the pump cell. Also disclosed is that an Au adsorbing layer that adsorbs Au atoms evaporated from the pump electrode is formed.

CITATION LIST

Patent Documents

Patent Document 1: JP3050781B2
Patent Document 2: JP2014-209128A
Patent Document 3: JP2014-190940A
Patent Document 4: JP6292735B2

SUMMARY OF THE INVENTION

Problems to be Solved by the Invention

In a conventional gas sensor, for example, as indicated in JP2014-209128A, oxygen that is generated by decomposition of a target gas to be measured is detected as a current value by a measurement pump cell in the condition that an oxygen partial pressure in a measurement-object gas is controlled to such a low oxygen partial pressure that does not substantially affect measurement of the target gas to be measured by a main pump cell and an auxiliary pump cell. That is, oxygen and the target gas to be measured in the measurement-object gas are separated from each other, and then oxygen that is generated from the target gas to be measured is measured.

In such a gas sensor, it is required that the target gas to be measured is not decomposed in the main pump cell. Therefore, a pump electrode that constitutes the main pump cell is made of a material that does not decompose the target gas to be measured (for example, NOx). As a material that does not decompose NOx, a metal material in which Au is added to Pt is known (JP2014-209128A, JP2014-190940A, JP6292735B2).

However, in such a conventional gas sensor, NOx output sometimes deteriorated due to a long term use. The present inventors made diligent efforts, and found that when the gas sensor is used for a long time under a high-temperature severe condition, Au included in the pump electrode constituting the main pump cell evaporates, and adheres to the measurement electrode constituting the measurement pump cell to possibly result in deterioration in NOx detection sensitivity.

Also, in a conventional gas sensor, it is assumed that the detectable concentration range of the target gas to be measured (for example, NOx) depends on the amount of the measurement-object gas reaching the measurement electrode. In other words, it is assumed that the detectable concentration range depends on a diffusion resistance from a gas inlet to a measurement electrode of a sensor element included in the gas sensor.

In the conventional gas sensor, for accurately measuring high concentration of NOx, the diffusion resistance of the sensor element may be high to limit the amount of the measurement-object gas that reaches the measurement electrode. This case however had the problem that the accuracy decreases in terms of S/N ratio for the measurement-object gas including low concentration of NOx.

As described above, in the conventional gas sensor, it was difficult to accurately measure both the measurement-object gas including high concentration of NOx, and the measurement-object gas including low concentration of NOx with a single gas sensor.

In the case of increasing the diffusion resistance of the sensor element so as to accurately measure high concentration of NOx, it is difficult in production of the sensor element to exactly control the diffusion resistance from the gas inlet to the measurement electrode of the sensor element to fall within a predetermined range. For example, in the case of adjusting the gas flow amount with a slit-like clearance, it is necessary to decrease the opening area of the slit so as to increase the diffusion resistance. The smaller the opening area, the more the variation in the opening area changes the value of diffusion resistance. Therefore, it is necessary to control the width and the thickness of the slit very precisely to manufacture a sensor element in which the diffusion resistance falls within a desired range. Such precise control is difficult in production to be achieved. Therefore, it was difficult to exactly control the diffusion resistance in the conventional gas sensor in terms of production and cost.

In light of the above, it is an object of the present invention to provide a sensor element capable of suppressing deterioration in detection accuracy of the gas sensor due to use and accurately measuring a measurement-object gas including a wide concentration range of a target gas to be measured, and a method for detecting a target gas to be measured using the sensor element.

Means for Solving the Problems

The present inventors found that by decomposing a target gas to be measured and removing a certain amount of a total oxygen in the measurement-object gas including an oxygen generated by decomposition in a target-gas-decomposing pump cell, and then detecting residual oxygen in a residual-oxygen-measuring pump cell, it is possible to suppress deterioration in detection accuracy of the gas sensor due to use, and it is possible to accurately measure a wide concentration range of the target gas to be measured.

The present invention includes the following aspects.

(1) A sensor element for detecting a target gas to be measured in a measurement-object gas, the sensor element comprising:
- a base part in an elongated plate shape, including a plurality of oxygen-ion-conductive solid electrolyte layers stacked;
- a measurement-object gas flow part for introduction and flow of a measurement-object gas through one end part in a longitudinal direction of the base part;
- a main pump cell including an inner main pump electrode disposed on an inner surface of the measurement-object gas flow part, and an outer pump electrode disposed at a position different from the measurement-object gas flow part on the base part and corresponding to the inner main pump electrode;
- a target-gas-decomposing pump cell including a target-gas-decomposing pump electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the target-gas-decomposing pump electrode;
- a residual-oxygen-measuring pump cell including a residual-oxygen-measuring electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the residual-oxygen-measuring electrode; and
- a reference electrode disposed inside the base part to be in contact with a reference gas, wherein the target-gas-decomposing pump electrode comprises a metal material that has catalytic activity of decomposing a target gas to be measured.

(2) The sensor element according to the above (1), wherein the residual-oxygen-measuring electrode comprises a metal material that does not have catalytic activity of decomposing the target gas to be measured.

(3) The sensor element according to the above (1) or (2), wherein the target-gas-decomposing pump electrode and the residual-oxygen-measuring electrode are disposed in this order in series in the longitudinal direction of the base part at positions farther from the one end part in the longitudinal direction of the base part than the inner main pump electrode on the inner surface of the measurement-object gas flow part.

(4) The sensor element according to the above (1) or (2), wherein the target-gas-decomposing pump electrode and the residual-oxygen-measuring electrode are disposed in parallel in the longitudinal direction of the base part at positions farther from the one end part in the longitudinal direction of the base part than the inner main pump electrode on the inner surface of the measurement-object gas flow part.

(5) The sensor element according to any one of the above (1) to (4), wherein the target-gas-decomposing pump electrode and a further oxygen-sensing electrode are disposed at positions farther from the one end part in the longitudinal direction of the base part than the inner main pump electrode on the inner surface of the measurement-object gas flow part, and
the sensor element further comprises an oxygen-partial-pressure-sensing cell including the oxygen-sensing electrode and the reference electrode.

(6) The sensor element according to any one of the above (1) to (5), wherein the target gas to be measured is NOx.

(7) The sensor element according to any one of the above (1) to (6), wherein the metal material included in the target-gas-decomposing pump electrode includes at least one selected from the group consisting of platinum and rhodium as a metal that has catalytic activity of decomposing the target gas to be measured.

(8) The sensor element according to any one of the above (1) to (7), wherein the metal material included in the target-gas-decomposing pump electrode does not include gold, or includes gold to the extent that catalytic activity of decomposing the target gas to be measured does not be inhibited.

(9) The sensor element according to any one of the above (1) to (8), wherein a metal material included in the residual-oxygen-measuring electrode includes platinum, and includes at least one selected from the group consisting of gold and silver as a metal that reduces catalytic activity of decomposing the target gas to be measured.

(10) The sensor element according to any one of the above (1) to (9), wherein a metal material included in the residual-oxygen-measuring electrode includes gold, and a content of the gold is 0.3% by weight or more in the metal material.

(11) The sensor element according to any one of the above (1) to (10), wherein at least two selected from the group consisting of the outer pump electrode corresponding to the inner main pump electrode, the outer pump electrode corresponding to the target-gas-decomposing pump electrode, and the outer pump electrode corresponding to the residual-oxygen-measuring electrode, are formed as an integrated electrode.

The present invention further includes a method for detecting a target gas to be measured in a measurement-object gas by using the sensor element according to any one of the above (1) to (11).

(12) A detection method of a target gas to be measured in a measurement-object gas using a sensor element, the sensor element comprising:
a base part in an elongated plate shape, including a plurality of oxygen-ion-conductive solid electrolyte layers stacked;
a measurement-object gas flow part for introduction and flow of a measurement-object gas through one end part in a longitudinal direction of the base part;
a main pump cell including an inner main pump electrode disposed on an inner surface of the measurement-object gas flow part, and an outer pump electrode disposed at a position different from the measurement-object gas flow part on the base part and corresponding to the inner main pump electrode;
a target-gas-decomposing pump cell including a target-gas-decomposing pump electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the target-gas-decomposing pump electrode;
a residual-oxygen-measuring pump cell including a residual-oxygen-measuring electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the residual-oxygen-measuring electrode; and
a reference electrode disposed inside the base part to be in contact with a reference gas,
wherein the target-gas-decomposing pump electrode comprises a metal material that has catalytic activity of decomposing a target gas to be measured, and
the detection method comprising:
an oxygen-concentration-adjusting step of adjusting an oxygen concentration in a measurement-object gas introduced into the measurement-object gas flow part to a predetermined concentration by the main pump cell, to obtain the measurement-object gas in which the oxygen concentration is adjusted to the predetermined concentration;
a current-value-controlling step of decomposing a target gas to be measured in the measurement-object gas on the target-gas-decomposing pump electrode by the target-gas-decomposing pump cell, and pumping out a predetermined constant amount of a total oxygen including an oxygen generated by decomposing the target gas to be measured in the measurement-object gas by the target-gas-decomposing pump cell so as to maintain a current value flowing through the target-gas-decomposing pump cell constant at a predetermined set value;
a detecting step of obtaining a detected current value that corresponds to a residual oxygen existed in the measurement-object gas flow part, by the residual-oxygen-measuring pump cell; and
a concentration-calculating step of calculating a concentration of the target gas to be measured based on the detected current value.

(13) The detection method according to the above (12), wherein, in the current-value-controlling step, the set value of the current value is determined by a total amount of a measurement-object gas that reaches the target-gas-decomposing pump electrode in the sensor element.

(14) The detection method according to the above (12) or (13), wherein the set value of the current value in the current-value-controlling step is set as a plurality of set values, and
the current value-controlling step further comprises a set-value-determining step of determining any set value to be used of the set values.

(15) The detection method according to the above (14), wherein, in the set-value-determining step, any set value to be used of the set values is determined based on a predicted concentration of a target gas to be measured in the measurement-object gas.

(16) The detection method according to any one of the above (12) to (15), wherein the metal material included in the target-gas-decomposing pump electrode includes gold, and
in the current-value-controlling step, an electromotive force between the target-gas-decomposing pump electrode and the reference electrode is controlled to a range from 350 mV to 500 mV.

Advantageous Effect of the Invention

According to the present invention, the electrode for obtaining a detected value, namely, the residual-oxygen-measuring electrode only has to have catalytic activity for oxygen, and need not have catalytic activity for the target gas to be measured. Even when the metal (for example, Au) that reduces the catalytic activity for the target gas to be measured included in the pump electrode evaporates, and the evaporated Au adheres to the residual-oxygen-measuring electrode, the catalytic activity for oxygen of the residual-oxygen-measuring electrode is maintained, so that the detection accuracy of the gas sensor does not deteriorate.

Thus, deterioration in detection accuracy of the gas sensor due to use of the gas sensor can be suppressed. In other words, according to the present invention, it is possible to suppress the change with time of the detected value of the target gas to be measured. As a result, the durability of the gas sensor improves.

Also, according to the present invention, the target gas to be measured is not directly detected. Instead, the target gas to be measured is decomposed and a certain amount of the total oxygen in the measurement-object gas including the oxygen generated by decomposition is removed in the target-gas-decomposing pump cell, and then residual oxygen in the measurement-object gas is detected in the residual-oxygen-measuring pump cell. The amount of oxygen removed in the target-gas-decomposing pump cell is correlated with the value of the pump current flowing through the target-gas-decomposing pump cell. Therefore, by the value of the pump current in the target-gas-decomposing pump cell, it is possible to adjust the range of the residual oxygen concentration reaching the residual-oxygen-measuring electrode. As a result, the gas sensor can be adapted even when the concentration of the target gas to be measured in the measurement-object gas largely varies. Thus, according to the present invention, it is possible to accurately measure the measurement-object gas including a wide concentration range of the target gas to be measured.

BRIEF DESCRIPTION OF THE DRAWINGS

FIG. 2 is a schematic view showing one example of a general planar arrangement of an inner main pump electrode 22, a target-gas-decomposing pump electrode 51, and a residual-oxygen-measuring electrode 44 disposed on a lower surface of a second solid electrolyte layer 6.

MODES FOR CARRYING OUT OF THE INVENTION

A sensor element of the present invention includes:
a base part in an elongated plate shape, including a plurality of oxygen-ion-conductive solid electrolyte layers stacked;
a measurement-object gas flow part for introduction and flow of a measurement-object gas through one end part in a longitudinal direction of the base part;
a main pump cell including an inner main pump electrode disposed on an inner surface of the measurement-object gas flow part, and an outer pump electrode disposed at a position different from the measurement-object gas flow part on the base part and corresponding to the inner main pump electrode;
a target-gas-decomposing pump cell including a target-gas-decomposing pump electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the target-gas-decomposing pump electrode;
a residual-oxygen-measuring pump cell including a residual-oxygen-measuring electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the residual-oxygen-measuring electrode; and
a reference electrode disposed inside the base part to be in contact with a reference gas,
wherein the target-gas-decomposing pump electrode comprises a metal material that has catalytic activity of decomposing a target gas to be measured.

The target gas to be measured is, for example, a gas component as included in exhaust gas of an internal combustion engine. Specific examples of the target gas to be measured include nitrogen oxide NOx, and ammonia $NH_3$.

[General Configuration of Gas Sensor]

Figure 1:
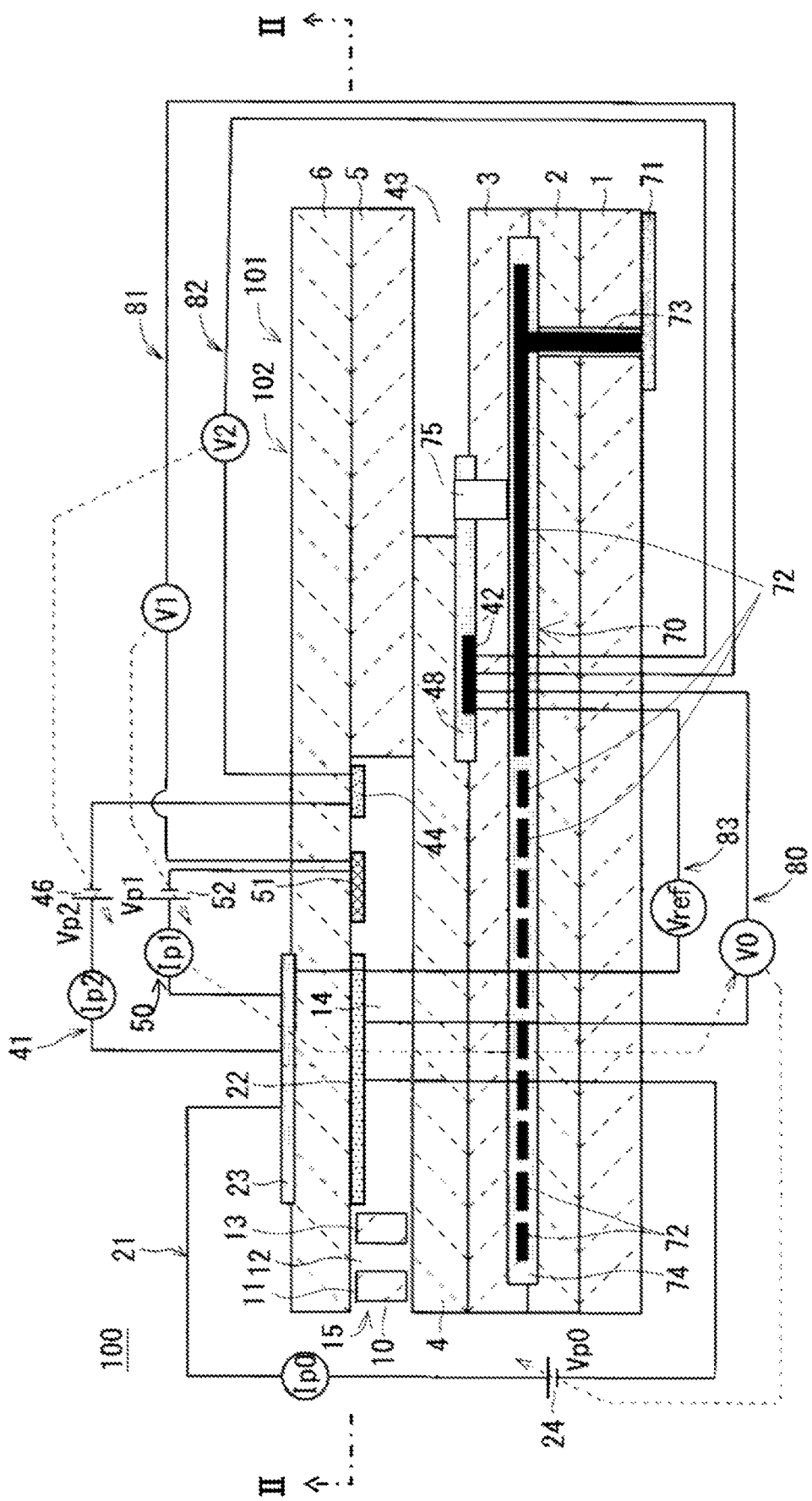
FIG. 1 is a vertical sectional schematic view in a longitudinal direction of a sensor element 101, showing one example of a general configuration of a gas sensor 100.

The sensor element of the present invention will now be described with reference to the drawings. FIG. 1 is a vertical sectional schematic view in the longitudinal direction, showing one example of a general configuration of a gas sensor 100 including a sensor element 101. Hereinafter, based on FIG. 1, the upper side and the lower side in FIG. 1 are respectively defined as top and bottom, and the left side and the right side in FIG. 1 are respectively defined as a front end side and a rear end side.

In the embodiment of FIG. 1, the gas sensor 100 represents one example of a limiting current type NOx sensor that detects NOx in a measurement-object gas by the sensor element 101, and measures the concentration of NOx.

The sensor element 101 is an element in an elongated plate shape, including a base part 102 having such a structure that a plurality of oxygen-ion-conductive solid electrolyte layers are layered. The elongated plate shape also called a long plate shape or a belt shape. The base part 102 has such a structure that six layers, namely, a first substrate layer 1, a second substrate layer 2, a third substrate layer 3, a first solid electrolyte layer 4, a spacer layer 5, and a second solid electrolyte layer 6, are layered in this order from the bottom side, as viewed in the drawing. Each of the six layers is formed of an oxygen-ion-conductive solid electrolyte layer containing, for example, zirconia ($ZrO_2$). The solid electrolyte forming these six layers is dense and gastight. These six layers all may have the same thickness, or the thickness may vary among the layers. The layers are adhered to each other with an adhesive layer of a solid electrolyte interposed therebetween, and the base part 102 includes the adhesive layer. While a layer configuration composed of the six layers is illustrated in FIG. 1, the layer configuration in the present invention is not limited to this, and any number of layers and any layer configuration are possible.

The sensor element 101 is manufactured, for example, by stacking ceramic green sheets corresponding to the individual layers after conducting predetermined processing, printing of circuit pattern and the like, and then firing the stacked ceramic green sheets so that they are combined together.

A gas inlet 10 is formed between the lower surface of the second solid electrolyte layer 6 and the upper surface of the first solid electrolyte layer 4 in one end part in the longitudinal direction (hereinafter, referred to as a front end part) of the sensor element 101. A measurement-object gas flow part 15 is formed in such a form that a first diffusion-rate limiting part 11, a buffer space 12, a second diffusion-rate limiting part 13, and an internal cavity 14 communicate in this order in the longitudinal direction from the gas inlet 10.

The gas inlet 10, the buffer space 12, and the internal cavity 14 constitute an internal space of the sensor element 101. The internal space is provided in such a manner that a portion of the spacer layer 5 is hollowed out, and the top of the internal space is defined by the lower surface of the second solid electrolyte layer 6, the bottom of the internal space is defined by the upper surface of the first solid electrolyte layer 4, and the lateral surface of the internal space is defined by the lateral surface of the spacer layer 5.

Each of the first diffusion-rate limiting part 11, and the second diffusion-rate limiting part 13 is provided as two laterally elongated slits (having the longitudinal direction of the openings in the direction perpendicular to the figure in FIG. 1). Each of the first diffusion-rate limiting part 11, and the second diffusion-rate limiting part 13 may be in such a form that a desired diffusion resistance is created, but the form is not limited to the slits.

Also, at a position farther from the front end than the measurement-object gas flow part 15, a reference gas introduction space 43 is disposed between the upper surface of the third substrate layer 3 and the lower surface of the spacer layer 5 at a position where the reference gas introduction space 43 is laterally defined by the lateral surface of the first solid electrolyte layer 4. The reference gas introduction space 43 has an opening in the other end part (hereinafter, referred to as a rear end part) of the sensor element 101. As a reference gas for NOx concentration measurement, for example, air is introduced into the reference gas introduction space 43.

An air introduction layer 48 is a layer formed of porous alumina, and is so configured that a reference gas is introduced into the air introduction layer 48 via the reference gas introduction space 43. The air introduction layer 48 is formed to cover a reference electrode 42.

The reference electrode 42 is an electrode sandwiched between the upper surface of the third substrate layer 3 and the first solid electrolyte layer 4, and as described above, the air introduction layer 48 leading to the reference gas introduction space 43 is disposed around the reference electrode 42. That is, the reference electrode 42 is disposed to be in contact with a reference gas via the air introduction layer 48 which is a porous material, and the reference gas introduction space 43. As will be described later, the reference electrode 42 can be used to measure the oxygen concentration (oxygen partial pressure) in the internal cavity 14.

In the measurement-object gas flow part 15, the gas inlet 10 is open to the external space, and the measurement-object gas is taken into the sensor element 101 from the external space through the gas inlet 10.

In the present embodiment, the measurement-object gas flow part 15 is in such a form that the measurement-object gas is introduced through the gas inlet 10 that is open on the front end surface of the sensor element 101, however, the present invention is not limited to this form. For example, the measurement-object gas flow part 15 need not have a recess of the gas inlet 10. In this case, the first diffusion-rate limiting part 11 substantially serves as a gas inlet.

For example, the measurement-object gas flow part 15 may have an opening that communicates with the buffer space 12 or a position in the vicinity of the buffer space 12 of the internal cavity 14, on a lateral surface along the longitudinal direction of the base part 102. In this case, the measurement-object gas is introduced from the lateral surface along the longitudinal direction of the base part 102 through the opening.

Further, for example, the measurement-object gas flow part 15 may be so configured that the measurement-object gas is introduced through a porous body.

The first diffusion-rate limiting part 11 creates a predetermined diffusion resistance to the measurement-object gas taken through the gas inlet 10.

The buffer space 12 is provided to guide the measurement-object gas introduced from the first diffusion-rate limiting part 11 to the second diffusion-rate limiting part 13.

The second diffusion-rate limiting part 13 creates a predetermined diffusion resistance to the measurement-object gas introduced into the internal cavity 14 from the buffer space 12.

It suffices that the amount of the measurement-object gas to be introduced into the internal cavity 14 falls within a predetermined range. That is, it suffices that a predetermined diffusion resistance is created in a whole from the front end part of the sensor element 101 to the second diffusion-rate limiting part 13. For example, the first diffusion-rate limiting part 11 may directly communicate with the internal cavity 14, or the buffer space 12 and the second diffusion-rate limiting part 13 may be absent.

The buffer space 12 is provided to mitigate the influence of pressure fluctuation on the detected value when the pressure of the measurement-object gas fluctuates.

When the measurement-object gas is introduced from outside the sensor element 101 into the internal cavity 14, the measurement-object gas, which is rapidly taken through the gas inlet 10 into the sensor element 101 due to pressure fluctuation of the measurement-object gas in the external space (pulsations in exhaust pressure if the measurement-object gas is automotive exhaust gas), is not directly introduced into the internal cavity 14. Rather, the measurement-object gas is introduced into the internal cavity 14 after the pressure fluctuation of the measurement-object gas is eliminated through the first diffusion-rate limiting part 11, the buffer space 12, and the second diffusion-rate limiting part 13. Thus, the pressure fluctuation of the measurement-object gas introduced into the internal cavity 14 becomes almost negligible.

The internal cavity 14 is provided as a space for detecting a target gas to be measured in the measurement-object gas introduced through the second diffusion-rate limiting part 13.

Figure 2:
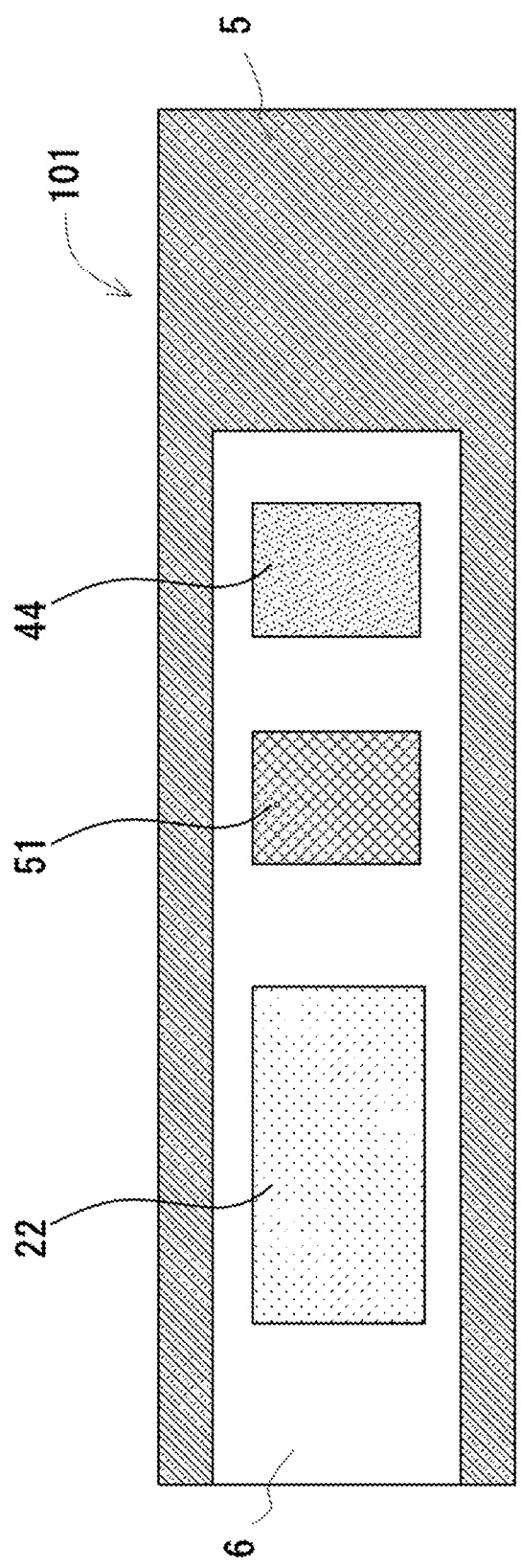
FIG. 2 is a sectional schematic view showing the section along line II-II in FIG. 1.

On the lower surface of the second solid electrolyte layer 6 facing with the internal cavity 14, an inner main pump electrode 22, a target-gas-decomposing pump electrode 51, and a residual-oxygen-measuring electrode 44 are disposed in series in this order in the longitudinal direction of the sensor element 101 from the position close to the front end part of the sensor element 101. FIG. 2 is a schematic view showing a general planar arrangement of the inner main pump electrode 22, the target-gas-decomposing pump electrode 51, and the residual-oxygen-measuring electrode 44 disposed on the lower surface of the second solid electrolyte layer 6. From each of the electrodes toward the rear end part of the sensor element 101, an electrode lead (not shown) is disposed to allow electric connection with the outside. In FIG. 2, these electrode leads are omitted in the drawing.

The main pump cell 21 is an electrochemical pump cell including an inner main pump electrode 22 disposed on an inner surface of the measurement-object gas flow part 15 and an outer pump electrode 23 disposed at a position different from the measurement-object gas flow part 15 on the base part 102 (in FIG. 1, on an outer surface of the base part 102) and corresponding to the inner main pump electrode 22. The phrase "corresponding to the inner main pump electrode 22" means that the outer pump electrode 23 and the inner main pump electrode 22 are provided with the second solid electrolyte layer 6 being interposed therebetween.

That is, the main pump cell 21 is an electrochemical pump cell composed of the inner main pump electrode 22 disposed at the position close to the front end part of the sensor element 101 on the lower surface of the second solid electrolyte layer 6 facing with the internal cavity 14, the outer pump electrode 23 disposed on a region of the upper surface of the second solid electrolyte layer 6 that corresponds to the inner main pump electrode 22 so as to be exposed to the external space, and the second solid electrolyte layer 6 sandwiched between the inner main pump electrode 22 and the outer pump electrode 23.

The inner main pump electrode 22 and the outer pump electrode 23 are formed as porous cermet electrodes (the electrode in a state that metal components and ceramic components are mixed). The ceramic component is not particularly limited, but an oxygen ion conductive solid electrolyte is preferably used as well as used in the base part 102. For example, as the ceramic component, $ZrO_2$ can be used. The metal component and the ceramic component in the porous cermet electrode may be appropriately determined by a person skilled in the art. For example, an amount of the ceramic component can be about 30% by weight to 50% by weight in the total of the metal component and the ceramic component. For example, when Pt is used as the metal component, and $ZrO_2$ is used as the ceramic component, the weight ratio of Pt:$ZrO_2$ may roughly be 7.0:3.0 to 5.0:5.0.

The main pump cell 21 is configured to be able to adjust the oxygen concentration in the measurement-object gas having flowed into the measurement-object gas flow part 15 to a predetermined concentration. Therefore, it is preferred that the inner main pump electrode 22 which is to come into contact with the measurement-object gas decompose only oxygen without reducing (decomposing) NOx components in the measurement-object gas. Specific constituting materials of the inner main pump electrode 22 will be described later.

In the main pump cell 21, a desired pump voltage $Vp0$ is applied between the inner main pump electrode 22 and the outer pump electrode 23 by a variable power supply 24 to flow a pump current $Ip0$ between the inner main pump electrode 22 and the outer pump electrode 23 in either a positive or negative direction, and thus it is possible to pump out oxygen in the vicinity of the inner main pump electrode 22 in the internal cavity 14 to the external space or pump oxygen into the internal cavity 14 from the external space.

To detect the oxygen concentration (oxygen partial pressure) in the atmosphere in the vicinity of the inner main pump electrode 22 in the internal cavity 14, the inner main pump electrode 22, the second solid electrolyte layer 6, the spacer layer 5, the first solid electrolyte layer 4, the third substrate layer 3, and the reference electrode 42 form an electrochemical sensor cell, namely, an oxygen-partial-pressure detection sensor cell 80 for main pump control.

The oxygen concentration (oxygen partial pressure) in the vicinity of the inner main pump electrode 22 in the internal cavity 14 can be detected from an electromotive force $V0$ measured in the oxygen-partial-pressure detection sensor cell 80 for main pump control. In addition, the pump current $Ip0$ is controlled by performing feedback control of the pump voltage $Vp0$ so that the electromotive force $V0$ is constant. Thus, the oxygen concentration in the vicinity of the inner main pump electrode 22 in the internal cavity 14 can be maintained at a predetermined constant value.

A target-gas-decomposing pump cell 50 is an electrochemical pump cell including the target-gas-decomposing pump electrode 51 disposed at a position farther from the front end part in the longitudinal direction of the base part 102 than the inner main pump electrode 22 on the inner surface of the measurement-object gas flow part 15, and the outer pump electrode 23 disposed at a position (in FIG. 1, the outer surface of the base part 102) different from the measurement-object gas flow part 15 in the base part 102 and corresponding to the target-gas-decomposing pump electrode 51. The phase "corresponding to the target-gas-decomposing pump electrode 51" means that the outer pump electrode 23 and the target-gas-decomposing pump electrode 51 are provided with the second solid electrolyte layer 6 being interposed therebetween.

That is, the target-gas-decomposing pump cell 50 is an electrochemical pump cell composed of the target-gas-decomposing pump electrode 51 disposed closer to the rear end of the sensor element 101 than the inner main pump electrode 22 on the lower surface of the second solid electrolyte layer 6 facing with the internal cavity 14, the outer pump electrode 23 (the outer electrode is not limited to the outer pump electrode 23, but may be any suitable electrode at a position different from that of the measurement-object gas flow part 15, e.g., outside the sensor element 101), and the second solid electrolyte layer 6.

The target-gas-decomposing pump cell 50 is configured to be capable of decomposing, in the target-gas-decomposing pump electrode 51, the target gas to be measured in the measurement-object gas in which oxygen concentration is kept at a predetermined constant value in the main pump cell 21, and discharging at least part of the total oxygen in the measurement-object gas including the oxygen generated by decomposition of the target gas to be measured from the measurement-object gas flow part 15. Therefore, the target-gas-decomposing pump electrode 51 is required to have catalytic activity of reducing (decomposing) NOx components in the measurement-object gas. Specific constituting materials of the target-gas-decomposing pump electrode 51 will be described later.

In the target-gas-decomposing pump cell 50, by applying a desired voltage $Vp1$ between the target-gas-decomposing pump electrode 51 and the outer pump electrode 23 by a variable power supply 52, it is possible to decompose NOx in the measurement-object gas having reached the target-gas-decomposing pump electrode 51, and pump out oxygen in the measurement-object gas including the oxygen generated by decomposition of NOx to the external space.

To control the oxygen partial pressure in the atmosphere in the vicinity of the target-gas-decomposing pump electrode 51 in the internal cavity 14, the target-gas-decomposing pump electrode 51, the reference electrode 42, the second solid electrolyte layer 6, the spacer layer 5, the first solid electrolyte layer 4, and the third substrate layer 3 constitute an electrochemical sensor cell, namely, an oxygen-partial-pressure detection sensor cell 81 for target-gas-decomposing pump control.

The auxiliary pump cell 50 performs pumping with the variable power supply 52 whose voltage is controlled on the basis of an electromotive force $V1$ detected by the oxygen-partial-pressure detection sensor cell 81 for target-gas-decomposing pump control. Thus, the oxygen partial pressure in the vicinity of the target-gas-decomposing pump electrode 51 in the internal cavity 14 is controlled to a lower partial pressure than the oxygen partial pressure in the vicinity of the inner main pump electrode 22 in the internal cavity 14.

In addition, a pump current Ip1 is used for control of the electromotive force V0 of the oxygen-partial-pressure detection sensor cell 80 for main pump control. Specifically, the pump current Ip1 is input to the oxygen-partial-pressure detection sensor cell 80 for main pump control as a control signal to control the electromotive force V0, and thus the gradient of the oxygen partial pressure in the measurement-object gas reached the target-gas-decomposing pump electrode 51 in the internal cavity 14 is controlled to remain constant.

A residual-oxygen-measuring pump cell 41 is an electrochemical pump cell including the r residual-oxygen-measuring electrode 44 disposed at a position farther from the front end part in the longitudinal direction of the base part 102 than the target-gas-decomposing pump electrode 51 on the inner surface of the measurement-object gas flow part 15, and the outer pump electrode 23 disposed at a position (in FIG. 1, the outer surface of the base part 102) different from the measurement-object gas flow part 15 in the base part 102 and corresponding to the residual-oxygen-measuring electrode 44. The phase "corresponding to the residual-oxygen-measuring electrode 44" means that the outer pump electrode 23 and the residual-oxygen-measuring electrode 44 are provided with the second solid electrolyte layer 6 being interposed therebetween.

That is, the residual-oxygen-measuring pump cell 41 is an electrochemical pump cell composed of the residual-oxygen-measuring electrode 44 disposed at a position farther from the front end part in the longitudinal direction of the sensor element 101 than the target-gas-decomposing pump electrode 51 on the lower surface of the second solid electrolyte layer 6 facing with the internal cavity 14, the outer pump electrode 23 (the outer electrode is not limited to the outer pump electrode 23, but may be any suitable electrode at a position different from that of the measurement-object gas flow part 15, e.g., outside the sensor element 101), and the second solid electrolyte layer 6.

The residual-oxygen-measuring pump cell 41 is configured to be capable of obtaining a detected current value corresponding to the concentration of the residual oxygen present in the measurement-object gas flow part 15. The measurement-object gas undergoes decomposition of NOx and discharge of a part of the total oxygen including the oxygen generated by decomposition in the target-gas-decomposing pump cell 50, and then reaches the residual-oxygen-measuring electrode 44. The residual-oxygen-measuring electrode 44 only have to be configured to be capable of detecting residual oxygen in the measurement-object gas. Specific constituting materials of the residual-oxygen-measuring electrode 44 will be described later.

To detect the oxygen partial pressure around the residual-oxygen-measuring electrode 44, the second solid electrolyte layer 6, the spacer layer 5, the first solid electrolyte layer 4, the third substrate layer 3, the residual-oxygen-measuring electrode 44, and the reference electrode 42 constitute an electrochemical sensor cell, namely an oxygen-partial-pressure detection sensor cell 82 for residual-oxygen-measuring pump control. A variable power supply 46 is controlled on the basis of an electromotive force V2 detected by the oxygen-partial-pressure detection sensor cell 82 for measurement pump control.

For the measurement-object gas introduced into the internal cavity 14, the oxygen partial pressure is controlled in the main pump cell 21, and the total oxygen including the oxygen generated by decomposition of NOx and the oxygen originally present in the measurement-object gas is partly pumped out in the target-gas-decomposing pump cell 50. Then, the measurement-object gas in which the rest of oxygen remains is to reach the residual-oxygen-measuring electrode 44. The residual oxygen in the measurement-object gas is to be pumped by the residual-oxygen-measuring pump cell 41, and at this time, a voltage Vp2 of the variable power supply 46 is controlled so that the control voltage V2 detected by the oxygen-partial-pressure detection sensor cell 82 for residual-oxygen-measuring pump control is constant.

A pump current Ip2 in the residual-oxygen-measuring pump cell 41 is proportional to the residual oxygen concentration in the measurement-object gas that reaches the vicinity of the residual-oxygen-measuring electrode 44. It is considered that the measurement-object gas that reaches the vicinity of the residual-oxygen-measuring electrode 44 is the same as the atmosphere in the vicinity of the target-gas-decomposing pump electrode 51 of the target-gas-decomposing pump cell 50 described above. As described above, the residual oxygen in the atmosphere in the vicinity of the target-gas-decomposing pump electrode 51, namely, the residual oxygen concentration in the measurement-object gas that reaches the residual-oxygen-measuring electrode 44 is correlated with the NOx concentration in the measurement-object gas. Therefore, the nitrogen oxide concentration in the measurement-object gas is calculated by using the pump current Ip2.

Also, the second solid electrolyte layer 6, the spacer layer 5, the first solid electrolyte layer 4, the third substrate layer 3, the outer pump electrode 23, and the reference electrode 42 constitute an electrochemical sensor cell 83, and it is possible to detect the oxygen partial pressure in the measurement-object gas outside the sensor by an electromotive force Vref obtained by the sensor cell 83.

In the gas sensor 100 having such a configuration, the measurement-object gas in which oxygen partial pressure is constantly kept at a constant low value by operating the main pump cell 21 is supplied to the target-gas-decomposing pump cell 50. The target-gas-decomposing pump cell 50 decomposes NOx in the measurement-object gas, and discharges a predetermined amount of the total oxygen in the measurement-object gas including the oxygen generated by decomposition to thereby control the flowing pump current to a constant current value. As a result, the residual oxygen concentration in the measurement-object gas that reaches the residual-oxygen-measuring electrode 44 is the concentration corresponding to the NOx concentration in the measurement-object gas. Therefore, in the residual-oxygen-measuring pump cell 41, the NOx concentration in the measurement-object gas can be recognized on the basis of the pump current Ip2 flowing as a result of pumping out the residual oxygen. Details of the control method using the sensor element 101 will be described later.

The sensor element 101 further includes a heater part 70 that functions as a temperature regulator of heating and maintaining the temperature of the sensor element 101 so as to enhance the oxygen ion conductivity of the solid electrolyte. The heater part 70 includes a heater electrode 71, a heater 72, a through hole 73, a heater insulating layer 74, and a pressure relief vent 75.

In the sensor element 101 of the present embodiment, the heater part 70 is embedded in the base part 102, but this form is not limitative. The heater 72 may be disposed to heat the base part 102. That is, the heater 72 may heat the sensor element 101 to develop oxygen ion conductivity with which the main pump cell 21, the target-gas-decomposing pump cell 50, and the residual-oxygen-measuring pump cell 41 are operable. For example, the heater part 70 may be embedded in the base part 102 as in the present embodiment. Alternatively, for example, the heater part 70 may be formed as a heater substrate that is separated from the base part 102, and may be disposed at a position adjacent to the base part 102. Alternatively, heating may be conducted by a measurement-object gas at high temperature. For accurate measurement, it is preferred that the temperature of the sensor element 101 be constant regardless of the temperature of the measurement-object gas. In consideration of this point, it is preferred that the sensor element 101 include the heater part 70 as in the present embodiment.

The heater electrode 71 is an electrode formed in contact with the lower surface of the first substrate layer 1. The power can be supplied to the heater part 70 from the outside by connecting the heater electrode 71 with an external power supply.

The heater 72 is an electrical resistor sandwiched by the second substrate layer 2 and the third substrate layer 3 from top and bottom. The heater 72 is connected with the heater electrode 71 via the through hole 73. The heater 72 is externally powered through the heater electrode 71 to generate heat, and heats and maintains the temperature of the solid electrolyte forming the sensor element 101.

The heater 72 is embedded over the whole area of the internal cavity 14 so that the temperature of the entire sensor element 101 can be adjusted to such a temperature that activates the solid electrolyte. The temperature may be adjusted so that the main pump cell 21, the target-gas-decomposing pump cell 50, and the residual-oxygen-measuring pump cell 41 are operable. It is not necessary that the whole area is adjusted to the same temperature, but the sensor element 101 may have temperature distribution.

The heater insulating layer 74 is formed of an insulator such as alumina on the upper and lower surfaces of the heater 72. The heater insulating layer 74 is formed to ensure electrical insulation between the second substrate layer 2 and the heater 72, and electrical insulation between the third substrate layer 3 and the heater 72.

The pressure relief vent 75 extends through the third substrate layer 3 so that the heater insulating layer 74 and the reference gas introduction space 43 communicate with each other. The pressure relief vent 75 can mitigate an increase in internal pressure due to temperature rise in the heater insulating layer 74. The pressure relief vent 75 may be absent.

(Constituting Material of Electrode)

Each of the inner main pump electrode 22, the target-gas-decomposing pump electrode 51 and the residual-oxygen-measuring electrode 44 is a porous cermet electrode (electrode in a form in which a metal component and a ceramic component are mixed). The ceramic component is not particularly limited, but an oxygen ion conductive solid electrolyte is preferably used as well as used in the base part 102. For example, as the ceramic component, $ZrO_2$ can be used. The metal component and the ceramic component in the porous cermet electrode may be appropriately determined by a person skilled in the art. For example, an amount of the ceramic component can be about 30% by weight to 50% by weight in the total of the metal component and the ceramic component. For example, when Pt is used as the metal component, and $ZrO_2$ is used as the ceramic component, the weight ratio of $Pt:ZrO_2$ may roughly be 7.0:3.0 to 5.0:5.0.

Hereinafter, metal materials in respective electrodes (the inner main pump electrode 22, the target-gas-decomposing pump electrode 51 and the residual-oxygen-measuring electrode 44) of the sensor element 101 will be specifically described.

(Inner Main Pump Electrode)

As described above, the main pump cell 21 is configured to be able to adjust the oxygen concentration in the measurement-object gas having flowed into the measurement-object gas flow part 15 to a predetermined concentration. Therefore, it is preferred that the inner main pump electrode 22 that is to come into contact with the measurement-object gas decompose only oxygen without reducing or decomposing the target gas to be measured (nitrogen oxide NOx, ammonia $NH_3$, or the like) in the measurement-object gas.

For example, as a metal material of the inner main pump electrode 22, a material based on platinum (Pt) to which a metal that reduces a catalytic activity of decomposing the target gas to be measured is added may be used.

Platinum (Pt) is a material that is widely used as a catalyst in general applications as well as in the field of gas sensor. Pt has a catalytic activity for oxygen, and a catalytic activity of decomposing the target gas to be measured (for example, NOx). By adding the metal that reduces the catalytic activity of decomposing the target gas to be measured to such Pt, it is expected that the catalytic activity of decomposing the target gas to be measured can be reduced while the catalytic activity to oxygen is maintained.

Examples of the metal that reduces the catalytic activity of decomposing NOx include gold (Au) and silver (Ag). It is considered that these metals do not have catalytic activity of decomposing NOx. Preferably, gold (Au) can be used.

The adding amount of the metal that decreases the catalytic activity of decomposing NOx may be appropriately set so that the inner main pump electrode 22 does not substantially decompose NOx. For example, when gold (Au) is added to platinum (Pt) which is a main component, Au may be added in an amount of 0.3% by weight or more relative to the total amount of the metal material. Preferably, Au may be added in an amount of 0.5% by weight or more. More preferably, Au may be added in an amount of 0.8% by weight or more. The adding amount of Au may be 3.0% by weight or less. Preferably, the adding amount of Au may be 2.0% by weight or less. By setting the adding amount of Au to fall within such a range, it is expected that the accuracy of measuring NOx concentration of the gas sensor 100 can be further improved. Also in the case of adding other metal such as Ag that decreases the catalytic activity of decomposing NOx, the aforementioned adding amount of Au can be referenced.

(Target-Gas-Decomposing Pump Electrode)

As described above, the target-gas-decomposing pump cell 50 is configured to be capable of decomposing, in the target-gas-decomposing pump electrode 51, the target gas to be measured in the measurement-object gas in which oxygen concentration is kept at a predetermined constant value in the main pump cell 21, and discharging at least part of the total oxygen in the measurement-object gas including the oxygen generated by decomposition of the target gas to be measured from the measurement-object gas flow part 15. Therefore, in the NOx sensor, the target-gas-decomposing pump electrode 51 is required to have catalytic activity of reducing (decomposing) NOx components in the measurement-object gas.

The target-gas-decomposing pump electrode 51 is a porous cermet electrode. The target-gas-decomposing pump electrode 51 constitutes the electrochemical pump cell, and also functions as a NOx reduction catalyst that reduces NOx present in the atmosphere in the internal cavity 14.

As a metal material of the target-gas-decomposing pump electrode 51, a noble metal material having a catalytic activity of decomposing NOx (reducing NOx) may be used. For example, platinum (Pt), rhodium (Rh) or the like may be used. For example, Pt may be used, or an alloy of Pt and Rh may be used. For example, when an alloy of Pt and Rh is used, Rh may be 10% by weight to 90% by weight in amount, relative to the total amount of Pt and Rh. By using noble metal having catalytic activity for NOx as a metal material of the target-gas-decomposing pump electrode 51, substantially all the NOx is decomposed in the target-gas-decomposing pump electrode 51, so that it is expected that high measurement accuracy is obtained.

The metal material of the target-gas-decomposing pump electrode 51 may not include gold, or may include gold in such a degree that the catalytic activity of decomposing the target gas to be measured is not inhibited. That is, as a metal material of the target-gas-decomposing pump electrode 51, a small amount of gold (Au) may be included in such a degree that catalytic activity for NOx develops.

For example, Au may be included in an amount of 0.3% by weight or less relative to the total of the metal material including Pt and Au. Preferably, Au may be included in an amount of 0.2% by weight or less. This is based on the premise that the amount of Au included in the target-gas-decomposing pump electrode 51 is smaller than the amount of Au included in the aforementioned inner main pump electrode 22. Also, the amount of Au included in the target-gas-decomposing pump electrode 51 may be the same with the amount of Au included in the later-described residual-oxygen-measuring electrode 44. Preferably, the amount of Au included in the target-gas-decomposing pump electrode 51 may be smaller than the amount of Au included in the residual-oxygen-measuring electrode 44.

Although Au substantially does not have catalytic activity of reducing NOx as described above, it is possible to decompose NOx in the target-gas-decomposing pump electrode 51 when the adding amount of Au is small. By the use of the gas sensor, even when Au evaporates from the inner main pump electrode 22, and adheres to the target-gas-decomposing pump electrode 51, it is considered that the change in activity of decomposing NOx is small because the target-gas-decomposing pump electrode 51 originally includes a small amount of Au. Therefore, even after using for a long time, the change in NOx sensitivity can be suppressed.

(Residual-Oxygen-Measuring Electrode)

As described above, the residual-oxygen-measuring pump cell 41 is configured to be capable of obtaining a detected current value corresponding to the concentration of the residual oxygen present in the measurement-object gas flow part 15. The measurement-object gas undergoes decomposition of NOx and discharge of a part of the total oxygen including the oxygen generated by decomposition in the target-gas-decomposing pump cell 50, and then reaches the residual-oxygen-measuring electrode 44. The residual-oxygen-measuring electrode 44 only have to be configured to be capable of detecting residual oxygen in the measurement-object gas.

The residual-oxygen-measuring electrode 44 is a porous cermet electrode. The residual-oxygen-measuring electrode 44 only have to have catalytic activity for oxygen ($O_2$). For example, platinum (Pt) may be used.

Even when Au in the inner main pump electrode 22 evaporates and the evaporated Au adheres to the residual-oxygen-measuring electrode 44 as a result of using the gas sensor for a long time under high oxygen concentration at a high temperature range, the activity for oxygen of the residual-oxygen-measuring electrode 44 is maintained, and thus the detection accuracy of the gas sensor does not deteriorate. Therefore, it is possible to suppress deterioration in detection accuracy of the gas sensor due to use. That is, the change with time of the NOx sensitivity can be suppressed. As a result, the durability of the gas sensor improves.

The target gas to be measured is decomposed in the aforementioned target-gas-decomposing pump cell 50. In the residual-oxygen-measuring pump cell 41, residual oxygen in the measurement-object gas is detected. By adjusting the pump current Ip1 in the target-gas-decomposing pump cell 50, it is possible to adjust the range of the residual oxygen concentration in the vicinity of the target-gas-decomposing pump electrode 51, namely, the residual oxygen concentration reaching the residual-oxygen-measuring electrode 44. Therefore, the gas sensor can be adapted even when the concentration of the target gas to be measured in the measurement-object gas largely varies. As a result, it is possible to accurately measure a wide concentration range of the target gas to be measured.

Preferably, the residual-oxygen-measuring electrode 44 is formed of a material that substantially lacks the ability to reduce a NOx component in the measurement-object gas or a material whose reducing ability is weakened. That is, it is preferred that the metal material of the residual-oxygen-measuring electrode 44 do not have catalytic activity of decomposing NOx. In this case, when part of NOx in the measurement-object gas is not decomposed in the target-gas-decomposing pump electrode 51 for some reason, and the gas including residual NOx reaches the residual-oxygen-measuring electrode 44, the residual NOx is not decomposed in the residual-oxygen-measuring electrode 44. It is considered that higher measurement accuracy is obtained by constantly detecting only the residual oxygen in the residual-oxygen-measuring electrode 44.

Specifically, as a metal material of the residual-oxygen-measuring electrode 44, a material based on platinum (Pt) to which a metal that reduces a catalytic activity of decomposing NOx is added may be used. Examples of the metal that reduces the catalytic activity of decomposing NOx include gold (Au) and silver (Ag). It is considered that these metals do not have catalytic activity of decomposing NOx. Preferably, gold (Au) can be used.

The adding amount of the metal that decreases the catalytic activity of decomposing NOx may be appropriately set so that the residual-oxygen-measuring electrode 44 does not substantially decompose NOx. For example, when gold (Au) is added to platinum (Pt) which is a main component, Au may be added in an amount of 0.3% by weight or more relative to the total amount of the metal material. Preferably, Au may be added in an amount of 0.5% by weight or more. More preferably, Au may be added in an amount of 0.8% by weight or more. The adding amount of Au may be 3.0% by weight or less. Preferably, the adding amount of Au may be 2.0% by weight or less. By setting the adding amount of Au to fall within such a range, it is expected that the accuracy of measuring residual oxygen can be further improved.

[Method for Producing Sensor Element]

Next, one example of a method for producing the sensor element as described above is described. A plurality of unfired sheet moldings (so-called green sheets) containing an oxygen-ion-conductive solid electrolyte such as zirconia ($ZrO_2$) as a ceramic component are subjected to a predetermined processing and printing of circuit pattern, and then the plurality of sheets are laminated, and the laminate was cut, and then fired. Thus the sensor element 101 can be manufactured.

Hereinafter, description is made while taking the case of manufacturing the sensor element 101 composed of six layers shown in FIG. 1 as an example.

First, six green sheets containing an oxygen-ion-conductive solid electrolyte such as zirconia ($ZrO_2$) as a ceramic component are prepared. For manufacturing of the green sheets, a known molding method can be used. The six green sheets may all have the same thickness, or the thickness differs depending on the layer to be formed. In each of the six green sheets, sheet holes or the like for use in positioning at the time of printing or stacking are formed in advance by a known method such as a punching process with a punching apparatus (blank sheet). In the blank sheet for use as the spacer layer 5, penetrating parts such as an internal cavity are also formed in the same manner. Also in the remaining layers, necessary penetrating parts are formed in advance.

The blank sheets for use as six layers, namely, the first substrate layer 1, the second substrate layer 2, the third substrate layer 3, the first solid electrolyte layer 4, the spacer layer 5, and the second solid electrolyte layer 6 are subjected to printing of various patterns required for respective layers and drying treatment. For printing of a pattern, a known screen printing technique can be used. Also as the drying treatment, a known drying means can be used.

In the case of forming the inner main pump electrode 22, the target-gas-decomposing pump electrode 51, and the residual-oxygen-measuring electrode 44, respective electrode pastes that provide the aforementioned desired electrode compositions are prepared.

Then, the electrode paste used for inner main pump electrode 22 is printed and dried in a desired pattern on the second solid electrolyte layer 6. Also, the electrode paste for the target-gas-decomposing pump electrode 51 is printed and dried in a desired pattern. Also, the electrode paste for the residual-oxygen-measuring electrode 44 is printed and dried in a desired pattern. The order of these printings may be appropriately determined.

After completing the printing and drying of diverse patterns for each of the six blank sheets by repeating these steps, contact bonding treatment of stacking the six printed blank sheets in a predetermined order while positioning with the sheet holes and the like, and contact bonding at a predetermined temperature and pressure condition to give a laminate is conducted. The contact bonding treatment is conducted by heating and pressurizing with a known laminator such as a hydraulic press. While the temperature, the pressure and the time of heating and pressurizing depend on the laminator being used, they may be appropriately determined to achieve excellent lamination.

The obtained laminate includes a plurality of sensor elements 101. The laminate is cut into units of the sensor element 101. The cut laminate is fired at a predetermined firing temperature to obtain the sensor element 101. The firing temperature may be such a temperature that the solid electrolyte forming the base part 102 of the sensor element 101 is sintered to become a dense product, and an electrode or the like maintains desired porosity. The firing is conducted, for example, at a firing temperature of about 1300 to 1500° C.

The obtained sensor element 101 is incorporated into the gas sensor 100 in such a form that the front end part of the sensor element 101 comes into contact with the measurement-object gas, and the rear end part of the sensor element 101 comes into contact with the reference gas.

[Detection Method]

Hereinafter, a method for detecting NOx using the aforementioned sensor element 101 will be specifically described.

A detection method of the present invention uses a sensor element, the sensor element including:
- a base part in an elongated plate shape, including a plurality of oxygen-ion-conductive solid electrolyte layers stacked;
- a measurement-object gas flow part for introduction and flow of a measurement-object gas through one end part in a longitudinal direction of the base part;
- a main pump cell including an inner main pump electrode disposed on an inner surface of the measurement-object gas flow part, and an outer pump electrode disposed at a position different from the measurement-object gas flow part on the base part and corresponding to the inner main pump electrode;
- a target-gas-decomposing pump cell including a target-gas-decomposing pump electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the target-gas-decomposing pump electrode;
- a residual-oxygen-measuring pump cell including a residual-oxygen-measuring electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the residual-oxygen-measuring electrode; and
- a reference electrode disposed inside the base part to be in contact with a reference gas, wherein the target-gas-decomposing pump electrode comprises a metal material that has catalytic activity of decomposing a target gas to be measured, and includes:
- an oxygen-concentration-adjusting step of adjusting an oxygen concentration in a measurement-object gas introduced into the measurement-object gas flow part to a predetermined concentration by the main pump cell, to obtain the measurement-object gas in which the oxygen concentration is adjusted to the predetermined concentration;
- a current-value-controlling step of decomposing a target gas to be measured in the measurement-object gas on the target-gas-decomposing pump electrode by the target-gas-decomposing pump cell, and pumping out a predetermined constant amount of a total oxygen including an oxygen generated by decomposing the target gas to be measured in the measurement-object gas by the target-gas-decomposing pump cell so as to maintain a current value flowing through the target-gas-decomposing pump cell constant at a predetermined set value;
- a detecting step of obtaining a detected current value that corresponds to a residual oxygen existed in the measurement-object gas flow part, by the residual-oxygen-measuring pump cell; and
- a concentration-calculating step of calculating a concentration of the target gas to be measured based on the detected current value.

In the oxygen-concentration-adjusting step, the oxygen concentration in the measurement-object gas flowed into the measurement-object gas flow part 15 is adjusted to a predetermined concentration, to obtain the measurement-object gas in which oxygen concentration is adjusted to the predetermined concentration. That is, the oxygen concentration (oxygen partial pressure) in the measurement-object gas flowed into the internal cavity 14 is controlled to be constant at a predetermined concentration by the main pump cell 21.

The pump voltage Vp0 of the variable power supply 24 in the main pump cell 21 is feedback controlled so that the electromotive force V0 in the oxygen-partial-pressure detection sensor cell 80 for main pump control is at a constant value (referred to as a set value $V0_{SET}$). The electromotive force V0 indicates the oxygen partial pressure in the vicinity of the inner main pump electrode 22, and therefore making the electromotive force V0 constant means that the oxygen partial pressure in the vicinity of the inner main pump electrode 22 is made constant. As a result, the pump current Ip0 in the main pump cell 21 varies depending on the oxygen concentration in the measurement-object gas.

When the oxygen partial pressure in the measurement-object gas is higher than the oxygen partial pressure corresponding to the set value $V0_{SET}$, the main pump cell 21 pumps oxygen out from the internal space 14. On the other hand, when the oxygen partial pressure in the measurement-object gas is lower than the oxygen partial pressure corresponding to the set value $V0_{SET}$ (for example, when hydrocarbons HC or the like are contained), the main pump cell 21 pumps oxygen into the internal space 14 from the space outside the sensor element 101. Therefore, the value of the pump current Ip0 may be either positive or negative.

In the current value-controlling step, by the target-gas-decomposing pump cell 50, the target gas to be measured in the measurement-object gas in which oxygen is adjusted to have a predetermined concentration is decomposed in the target-gas-decomposing pump electrode 51, and a predetermined constant amount of the total oxygen including the oxygen generated by decomposition of the target gas to be measured in the measurement-object gas is pumped out from the measurement-object gas flow part 15 so that the current value flowing through the target-gas-decomposing pump cell 50 is kept constant at a predetermined set value. That is, NOx in the measurement-object gas in which oxygen partial pressure is adjusted by the main pump cell 21 is decomposed, and a constant amount of the total oxygen including the oxygen generated by decomposition and the oxygen in the atmosphere gas is pumped out to control the pump current value constant.

The pump voltage Vp1 of the variable power supply 52 in the target-gas-decomposing pump cell 50 is feedback controlled so that the electromotive force V1 detected by the oxygen-partial-pressure detection sensor cell 81 for target-gas-decomposing pump control is a constant value (referred to as a set value $V1_{SET}$). Since the electromotive force V1 shows the oxygen partial pressure in the vicinity of the target-gas-decomposing pump electrode 51, keeping the electromotive force V1 constant means keeping the oxygen partial pressure in the vicinity of the target-gas-decomposing pump electrode 51 constant. The set value $V1_{SET}$ can be set as a value that gives a low oxygen concentration at which NOx in the measurement-object gas can be sufficiently decomposed.

The set value $V1_{SET}$ of the electromotive force V1 may be, for example, 350 mV to 500 mV. Preferably, the set value $V1_{SET}$ may be 380 mV to 430 mV.

When the target-gas-decomposing pump electrode 51 includes a small amount of Au, it is assumed that catalytic activity for NOx in the target-gas-decomposing pump electrode 51 is slightly suppressed. It is however expected that NOx can be decomposed better by increasing the electromotive force V1. That is, this indicates that the decomposition amount of the target gas to be measured in the target-gas-decomposing pump electrode 51 can be controlled to a desired range by controlling the electromotive force V1. When the target-gas-decomposing pump electrode 51 includes a small amount of Au, the set value $V1_{SET}$ may be, for example, 350 mV to 500 mV. Preferably, the set value $V1_{SET}$ may be 400 mV to 480 mV.

When the electromotive force V1 is increased, the pump voltage Vp1 applied between the target-gas-decomposing pump electrode 51 and the outer pump electrode 23 also increases according to the electromotive force V1. In a so-called limiting current region, the flowing pump current Ip1 is substantially constant even when the pump voltage Vp1 increases. However, it is expected that the larger the electromotive force V1 (or the pump voltage Vp1), the more the decomposition of NOx can be promoted in the target-gas-decomposing pump electrode 51. That is, it is expected that almost all the NOx can be decomposed, and the measurement accuracy improves.

The measurement-object gas introduced into the internal cavity 14 is to reach the target-gas-decomposing pump electrode 51 after the oxygen partial pressure is controlled in the main pump cell 21. Nitrogen oxide (NOx) in the measurement-object gas around the target-gas-decomposing pump electrode 51 is reduced (2NO→N$_2$+O$_2$) to generate oxygen. Then the generated oxygen and the oxygen in the measurement-object gas of which oxygen partial pressure has been controlled by the main pump cell 21 is to be pumped by the target-gas-decomposing pump cell 50. At this time, the voltage Vp1 of the variable power supply 52 is controlled so that the control voltage V1 detected by the oxygen-partial-pressure detection sensor cell 81 for target-gas-decomposing pump control is constant.

Also conducted is a feedback control of setting a set value $V0_{SET}$ of the electromotive force V0 on the basis of the pump current Ip1 in the target-gas-decomposing pump cell 50 so that the pump current Ip1 is a constant value (referred to as a set value $Ip1_{SET}$). As a result, the oxygen partial pressure in the measurement-object gas to reach the target-gas-decomposing pump electrode 51 is constant.

As described above, the measurement-object gas reaches the target-gas-decomposing pump electrode 51 in the condition that the oxygen partial pressure has been controlled in the main pump cell 21. That is, an oxygen partial pressure P(O$_2$) in the measurement-object gas at the time of reaching the target-gas-decomposing pump electrode 51 is kept constant.

In the target-gas-decomposing pump electrode 51, NOx in the measurement-object gas is decomposed (2NO→N$_2$+O$_2$) to generate oxygen. The generated oxygen partial pressure is denoted by P(NOx).

As a result, the oxygen partial pressure in the vicinity of the target-gas-decomposing pump electrode 51 is a total amount [P(Total)=P(O$_2$)+P(NOx)] of:
 a partial pressure of oxygen originally present in the measurement-object gas [P(O$_2$)=constant] and a partial pressure of oxygen generated by
 decomposition of NOx [P(NOx)=amount corresponding to NOx concentration].

That is, the oxygen amount in the vicinity of the target-gas-decomposing pump electrode 51 varies depending on the NOx concentration in the measurement-object gas.

The total amount of the measurement-object gas that reaches the target-gas-decomposing pump electrode 51 depends on the diffusion resistance from the gas inlet 10 to the target-gas-decomposing pump electrode 51. The diffusion resistance is substantially equal to the diffusion resistance created by the first diffusion-rate limiting part 11 and the second diffusion-rate limiting part 13. The oxygen partial pressure being constant is synonymous with the oxygen amount (number of oxygen molecules) being constant.

As described above, the pump current Ip1 in the target-gas-decomposing pump cell 50 is controlled to be a constant value (set value $Ip1_{SET}$). The pump current Ip1 is directly correlated with the oxygen amount having moved in the target-gas-decomposing pump cell 50. That is, controlling the pump current Ip1 to a constant value (set value $Ip1_{SET}$) means constantly pumping out a constant amount [indicated by $P(Ip1_{SET})$] of the oxygen amount in the measurement-object gas having reached the target-gas-decomposing pump electrode 51. As a result, part of the oxygen remains in the vicinity of the target-gas-decomposing pump electrode 51. The residual oxygen partial pressure [indicated by P(R)] is represented by the following formula (1).

$$P(R)=P(O_2)+P(NOx)-P(Ip1_{SET}) \quad (1)$$

Here, as described above, $P(O_2)$ and $P(Ip1_{SET})$ each are a constant value, and P(NOx) is an amount corresponding to the NOx concentration in the measurement-object gas. Therefore, the residual oxygen amount [P(R)] is expected to be an amount corresponding to the NOx concentration in the measurement-object gas.

From the viewpoint of the current value, the following consideration can be made. It is considered that the pump current Ip1 in the target-gas-decomposing pump cell 50 is composed of a pump current Ip(NOx) for pumping the oxygen generated by reduction of NOx, and a pump current $Ip(O_2)$ for pumping oxygen in the measurement-object gas of which oxygen partial pressure has been controlled by the main pump cell 21, as shown in the following formula (2). While Ip(NOx) and $Ip(O_2)$ are described separately for convenience of description, the currents cannot be detected separately as actual pump currents.

$$Ip1=Ip(NOx)+Ip(O_2)=constant \quad (2)$$

As described above, since the pump current Ip1 is controlled to be a constant value, oxygen corresponding to the magnitude of Ip(NOx) remains as residual oxygen in the measurement-object gas in the vicinity of the target-gas-decomposing pump electrode 51 as determined from the relationship of the formula (2).

When the NOx concentration in the measurement-object gas is high, the pump current Ip(NOx) for pumping the oxygen generated by reduction of NOx increases, and on the other hand, the pump current $Ip(O_2)$ for pumping part of the oxygen in the measurement-object gas of which oxygen partial pressure is controlled by the main pump cell 21 decreases. As a result, the residual oxygen concentration in the atmosphere in the vicinity of the target-gas-decomposing pump electrode 51 increases.

On the contrary, when the NOx concentration in the measurement-object gas is low, the pump current Ip(NOx) for pumping the oxygen generated by reduction of NOx decreases, and on the other hand, the pump current $Ip(O_2)$ for pumping part of the oxygen in the measurement-object gas of which oxygen partial pressure is controlled by the main pump cell 21 increases. As a result, the residual oxygen concentration in the atmosphere in the vicinity of the target-gas-decomposing pump electrode 51 decreases.

Thus, the residual oxygen concentration in the atmosphere in the vicinity of the target-gas-decomposing pump electrode 51 increases when the NOx concentration in the measurement-object gas increases and decreases when the NOx concentration in the measurement-object gas decreases. That is, the residual oxygen concentration in the atmosphere in the vicinity of the target-gas-decomposing pump electrode 51 is correlated with the NOx concentration in the measurement-object gas.

Also, as described above, the pump current Ip1 is controlled to a constant value. Therefore, even when Au adheres to the target-gas-decomposing pump electrode 51, and catalytic activity for the target gas to be measured slightly decreases, it is possible to decompose the target gas to be measured in the target-gas-decomposing pump electrode 51 by the pump voltage Vp1 applied to keep the pump current Ip1 constant. Therefore, it is possible to suppress deterioration in detection accuracy of the gas sensor due to use of the detection electrode. That is, it is possible to suppress the change with time of the detected value of the target gas to be measured. As a result, the durability of the gas sensor improves.

The set value $Ip1_{SET}$ of the pump current Ip1 may be appropriately set to pump out oxygen derived from the target gas to be measured (NOx in the present embodiment). For example, the set value $Ip1_{SET}$ may be 1 µA to 15 µA. Preferably, the set value $Ip1_{SET}$ may be 3 µA to 10 µA. For example, the set value $Ip1_{SET}$ may be 7 µA.

It is preferred that the set value $Ip1_{SET}$ be a current value of not less than Ip(NOx) that is to flow according to the NOx amount in the measurement-object gas. It is expected that such a set value will not cause saturation of the residual oxygen concentration. It is expected that by the set value within such a range, an exact NOx concentration can be detected particularly when NOx concentration is high.

It is preferred that the set value $Ip1_{SET}$ be not too large compared with Ip(NOx) that is to flow according to the NOx amount in the measurement-object gas. With such a set value, it would be possible to make the S/N ratio fall within an appropriate range, and detect an exact NOx concentration in the later-described detecting step particularly when NOx concentration is low.

For example, the set value $Ip1_{SET}$ may be set on the basis of the total amount of the measurement-object gas that reaches the target-gas-decomposing pump electrode 51. The total amount of the measurement-object gas that reaches the target-gas-decomposing pump electrode 51 depends on the diffusion resistance from the measurement-object gas inlet 10 to the target-gas-decomposing pump electrode 51 of the sensor element 101.

For example, a relation between the diffusion resistance and the optimum set value $Ip1_{SET}$ is determined in advance. For the sensor element 101, a diffusion resistance from the measurement-object gas inlet 10 to the target-gas-decomposing pump electrode 51 is measured, and the set value $Ip1_{SET}$ can be determined according to the value of the diffusion resistance.

Alternatively, the set value $Ip1_{SET}$ may be determined by using a value of diffusion resistance from the measurement-object gas inlet 10 to the inner main pump electrode 22. It is assumed that the value of diffusion resistance from the measurement-object gas inlet 10 to the inner main pump electrode 22 corresponds to the amount of the measurement-object gas flowing into the measurement-object gas flow part 15.

By determining the set value $Ip1_{SET}$ in this manner, it is possible to prevent the detected current value from causing saturation and make the S/N ratio fall within an appropriate range, and therefore to obtain a detected current value with high accuracy in the later-described detecting step.

In a current value constantly controlling step, a set value determining step may further be included. Here, the set value $Ip1_{SET}$ may be variable. That is, a plurality of set values $Ip1_{SET}$ are set in advance, and a control of appropriately changing the set value during use of the gas sensor 100 (during measurement of the target gas to be measured) may be conducted. In this case, in the set-value-determining step, which set value $Ip1_{SET}$ of the plurality of set values $Ip1_{SET}$ is to be used in the current value-controlling step is determined. The plurality of set values $Ip1_{SET}$ may be switched over stepwise, or the set values $Ip1_{SET}$ may be changed sequentially.

For example, when the NOx concentration in the measurement-object gas is high, it is conceivable to prevent the detected value in the later-described detecting step from saturating by increasing the set value $Ip1_{SET}$. On the other hand, when the NOx concentration in the measurement-object gas is low, it is conceivable to increase the S/N ratio by decreasing the set value $Ip1_{SET}$.

In the case of changing the set value $Ip1_{SET}$ according to the NOx concentration in the measurement-object gas, a control of predicting the NOx concentration in the measurement-object gas, and switching over the set value $Ip1_{SET}$ according to the predicted NOx concentration may be conducted. That is, in the set-value-determining step, which set value of the plurality of set values is to be used may be determined according to the predicted concentration of the target gas to be measured in the measurement-object gas.

When the measurement-object gas is an emission gas of automobiles, the amount of NOx to be generated can be estimated from the conditions such as engine speed, temperature of the emission gas and concentration of the hydrocarbon (HC). For example, the relation (map) between the conditions such as engine speed, temperature of emission gas and concentration of hydrocarbon (HC), and the NOx concentration in the emission gas is prepared in advance. The data such as engine speed, temperature of emission gas and concentration of hydrocarbon (HC) is acquired during measurement, and it can be estimated from the map whether the NOx concentration in the measurement-object gas is low concentration or high concentration. In the set-value-determining step, when the NOx concentration is estimated as low concentration, a set value for low concentration $Ip1_{SET}$ (Low) may be applied, whereas when the NOx concentration is estimated as high concentration, a set value for high concentration $Ip1_{SET}$ (High) may be applied.

In the detecting step, a detected current value corresponding to the concentration of the residual oxygen present in the measurement-object gas flow part 15 is obtained by the residual-oxygen-measuring pump cell 41. That is, the residual oxygen in the measurement-object gas is detected as the pump current Ip2.

The pump voltage Vp2 of the variable power supply 46 in the residual-oxygen-measuring pump cell 41 is feedback controlled so that the electromotive force V2 detected by the oxygen-partial-pressure detection sensor cell 82 for residual-oxygen-measuring pump control is a constant value (referred to as a set value $V2_{SET}$). Since the electromotive force V2 shows the oxygen partial pressure in the vicinity of the residual-oxygen-measuring electrode 44, keeping the electromotive force V2 constant means keeping the oxygen partial pressure in the vicinity of the residual-oxygen-measuring electrode 44 constant. The set value $V2_{SET}$ can be set as a value that makes the oxygen partial pressure in the vicinity of the residual-oxygen-measuring electrode 44 substantially zero.

By the residual-oxygen-measuring pump cell 41, the residual oxygen in the measurement-object gas is pumped out so that the oxygen partial pressure in the vicinity of the residual-oxygen-measuring electrode 44 is substantially zero. The pump current Ip2 in the residual-oxygen-measuring pump cell 41 at this time is detected. The pump current Ip2 is referred to as a detected current value.

The temperature in the vicinity of the residual-oxygen-measuring electrode 44 may be kept lower than the temperature in the vicinity of the inner main pump electrode 22. For example, 750° C. or less is preferred.

When the temperature in the vicinity of the residual-oxygen-measuring electrode 44 is low, Au included in the residual-oxygen-measuring electrode 44 is difficult to evaporate, and recrystallization of Pt after oxidization and evaporation is also suppressed. Therefore, even after using for a long time, it is possible to prevent NOx from decomposing in the residual-oxygen-measuring electrode 44. Therefore, even after using for a long time, it is possible to measure only the residual oxygen more accurately in the residual-oxygen-measuring electrode 44. As a result, the durability of the gas sensor further improves.

In the concentration-calculating step, NOx concentration in the measurement-object gas is calculated from the detected current value.

The value of the detected pump current Ip2 (detected current value) corresponds to the amount of the residual oxygen in the measurement-object gas. The amount of the residual oxygen in the measurement-object gas corresponds to the NOx concentration in the measurement-object gas, as described above. As a result, the pump current Ip2 and the NOx concentration in the measurement-object gas are correlated. On the basis of the correlation, the NOx concentration in the measurement-object gas is calculated from the pump current Ip2 (detected current value).

It is assumed that the correlation between the pump current Ip2 and the NOx concentration in the measurement-object gas differs depending on the set value $Ip1_{SET}$ in the current value constantly controlling step described above. Therefore, when a plurality of set values $Ip1_{SET}$ are used, the correlation is examined in advance for each of the set values $Ip1_{SET}$, and the NOx concentration in the measurement-object gas is calculated from the pump current Ip2 (detected current value) on the basis of the correlation in accordance with each of the set values $Ip1_{SET}$.

In the above embodiment, the case of detecting NOx is described. For example, when ammonia $NH_3$ is a target gas to be measured, ammonia $NH_3$ in the measurement-object gas introduced into the internal cavity 14 may be oxidized to be NO in the main pump cell 21. Then, ammonia $NH_3$ can be detected by detecting NO as described in the above embodiment.

In the above embodiment, the form in which the inner main pump electrode 22, the target-gas-decomposing pump electrode 51, and the residual-oxygen-measuring electrode 44 are disposed in series in the longitudinal direction of the sensor element 101 from the front end part toward the rear end part of the sensor element 101 on the lower surface of the second solid electrolyte layer 6 facing with the first internal cavity 14 is shown, however, the present invention is not limited to this form.

[Variation 1 of Present Invention]

Figure 3:
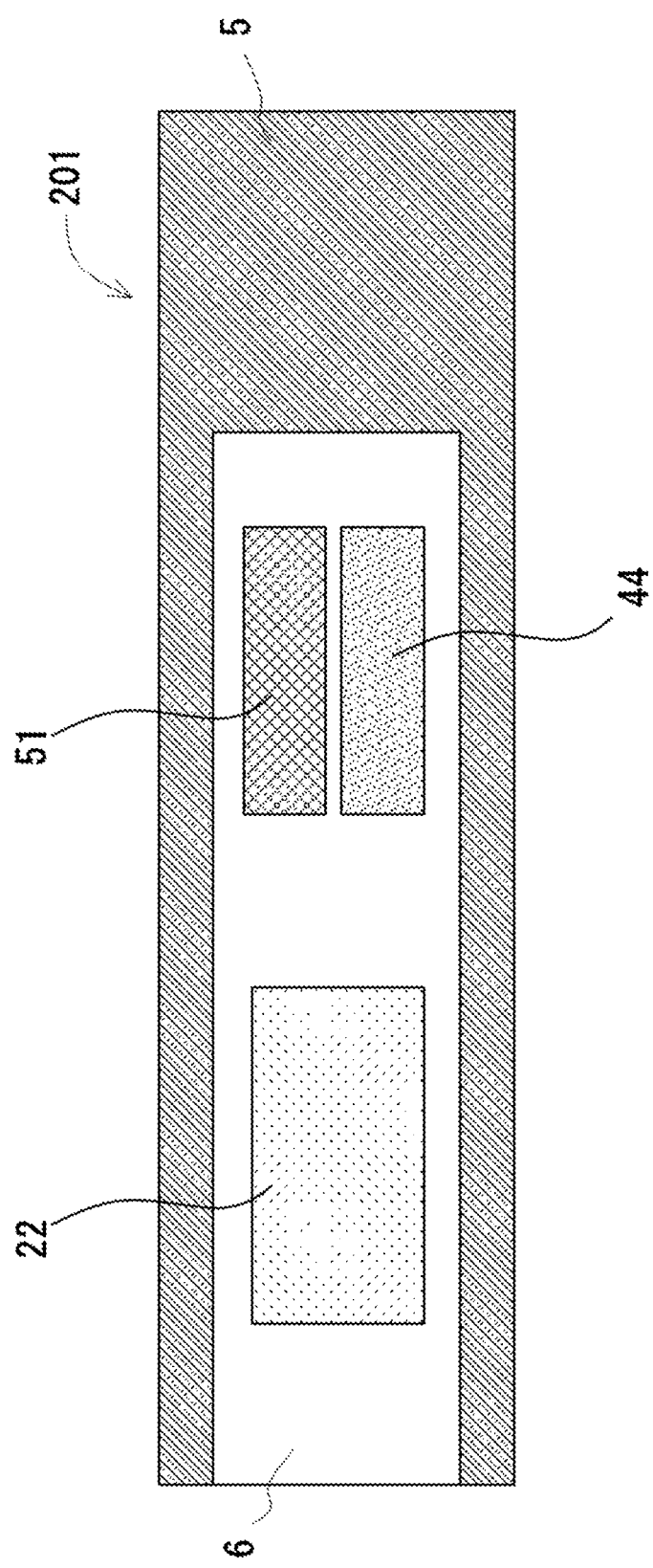
FIG. 3 is a schematic view showing another example (a sensor element 201) of a general planar arrangement of an inner main pump electrode 22, a target-gas-decomposing pump electrode 51, and a residual-oxygen-measuring electrode 44 disposed on a lower surface of a second solid electrolyte layer 6.

In a sensor element 201 of Variation 1, on the lower surface of the second solid electrolyte layer 6 facing with the one internal cavity 14, the inner main pump electrode 22 is disposed on the side close to the front end part of the sensor element 201, and the target-gas-decomposing pump electrode 51 and the residual-oxygen-measuring electrode 44 are disposed in parallel in the longitudinal direction of the sensor element 201 at positions farther from the front end part of the sensor element 201 than the inner main pump electrode 22. FIG. 3 is a schematic view showing a general planar arrangement of the inner main pump electrode 22, the target-gas-decomposing pump electrode 51, and the residual-oxygen-measuring electrode 44 disposed on the lower surface of the second solid electrolyte layer 6 in the sensor element 201 of Variation 1. From each electrode toward the rear end of the element, an electrode lead is disposed to allow connection with the outside. In FIG. 3, these electrode leads are omitted in the drawing as with the case of FIG. 2.

In the sensor element 201 of Variation 1, in the main pump cell 21, the oxygen concentration in the vicinity of the inner main pump electrode 22 in the internal cavity 14 is kept at a predetermined constant value, and the measurement-object gas of which oxygen is adjusted to the predetermined concentration simultaneously reaches both the target-gas-decomposing pump electrode 51 and the residual-oxygen-measuring electrode 44 that are disposed in parallel.

In the sensor element 201 of Variation 1, the residual-oxygen-measuring electrode 44 is kept exposed to the gas including NOx. In such a case, it is presumable that part of NOx is decomposed in the residual-oxygen-measuring electrode 44. Considering this point, it is assumed that the serial electrode arrangement as in the sensor element 101 of the above embodiment is more preferred.

[Variation 2 of Present Invention]

Figure 4:
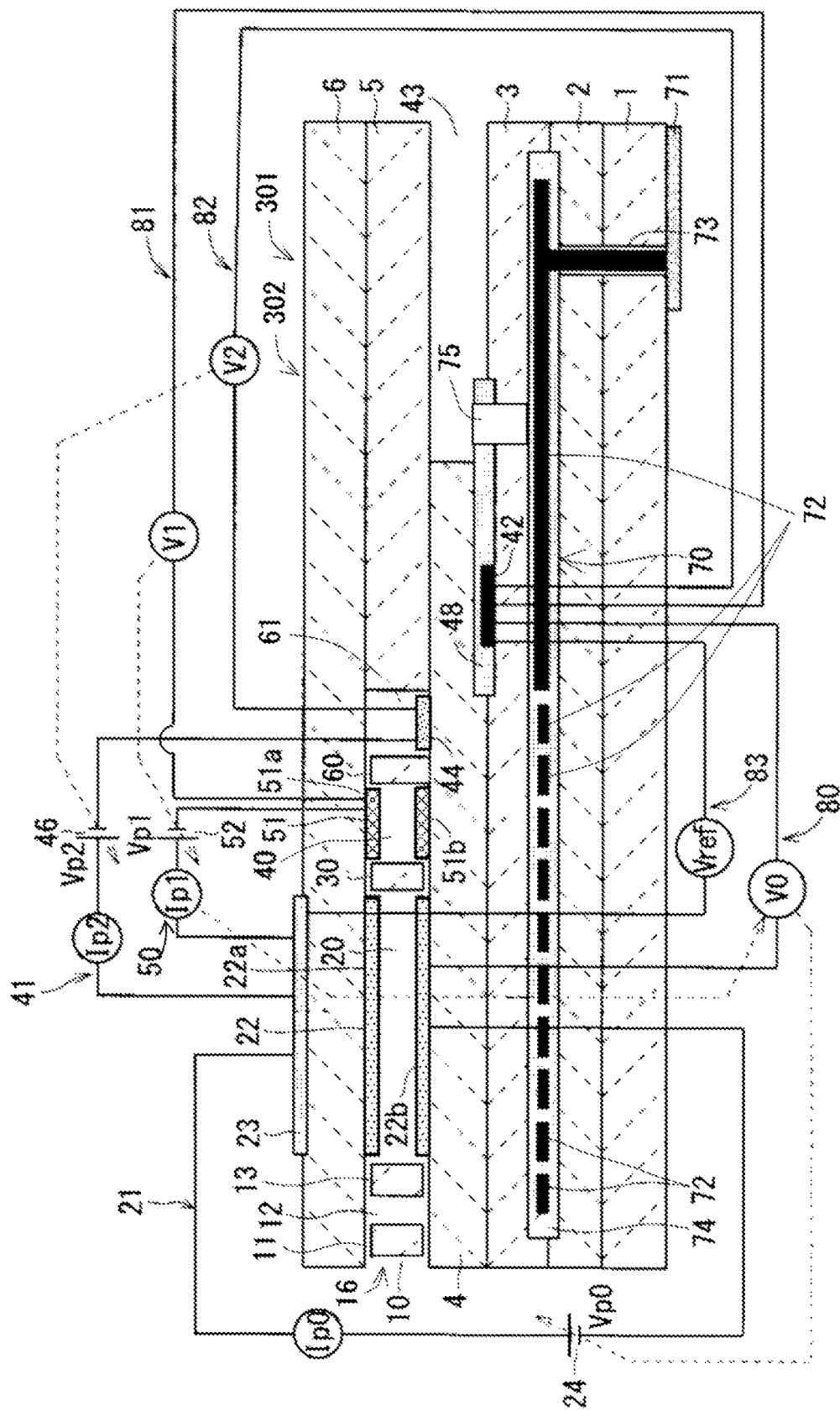
FIG. 4 is a vertical sectional schematic view in the longitudinal direction of a sensor element 301, showing another example of a gas sensor 100.

FIG. 4 is a vertical sectional schematic view of a sensor element 301 of Variation 2 in the longitudinal direction of the sensor element 301. In FIG. 4, the same member as in FIG. 1 is denoted by the same sign, and description of the same member is omitted.

In the sensor element 301 of Variation 2, the inner main pump electrode 22 is disposed to face with a first internal cavity 20, the target-gas-decomposing pump electrode 51 is disposed to face with a second internal cavity 40, and the residual-oxygen-measuring electrode 44 is disposed to face with a third internal cavity 61. That is, the individual internal cavities that communicate with each other via a diffusion-rate limiting part each are provided with respective one electrode.

In the sensor element 301 of Variation 2, a measurement-object gas flow part 16 is formed in such a form that the first diffusion-rate limiting part 11, the buffer space 12, the second diffusion-rate limiting part 13, the first internal cavity 20, a third diffusion-rate limiting part 30, the second internal cavity 40, a fourth diffusion-rate limiting part 60, and the third internal cavity 61 communicate in this order in the longitudinal direction from the gas inlet 10.

In the sensor element 301 of Variation 2, the third diffusion-rate limiting part 30 is provided as two laterally elongated slits (having the longitudinal direction of the openings in the direction perpendicular to the figure in FIG. 3). The fourth diffusion-rate limiting part 60 is provided as a single laterally elongated slit (having the longitudinal direction of the opening in the direction perpendicular to the figure in FIG. 3) between the spacer layer 5 and the second solid electrolyte layer 6. Each of the third diffusion-rate limiting part 30 and the fourth diffusion-rate limiting part 60 may be in such a form that a desired diffusion resistance is created, but the form is not limited to the slits.

In the sensor element 301 of Variation 2, the inner main pump electrode 22 is formed to span the upper and lower solid electrolyte layers (the second solid electrolyte layer 6 and the first solid electrolyte layer 4) that define the first internal cavity 20 and the spacer layer 5 that defines the lateral wall. Specifically, the ceiling electrode portion 22a is formed on substantially the entire surface of the lower surface of the second solid electrolyte layer 6 that defines the ceiling surface of the first internal cavity 20, and a bottom electrode portion 22b is formed on substantially the entire surface of the upper surface of the first solid electrolyte layer 4 that defines the bottom surface of the first internal cavity 20. Also, lateral electrode portions (not shown) are formed on the lateral wall surfaces (inner surface) of the spacer layer 5 that form both lateral wall parts of the first internal cavity 20 so as to connect the ceiling electrode portion 22a and the bottom electrode portion 22b. Thus, the inner main pump electrode 22 is provided as a tunnel-like structure in the area where the lateral electrode portions are disposed.

In the sensor element 301 of Variation 2, the target-gas-decomposing pump electrode 51 is disposed in the second internal cavity 40 in a tunnel-like structure similar to the inner main pump electrode 22 disposed in the first internal cavity 20. Specifically, in the tunnel-like structure, the ceiling electrode portion 51a is formed on substantially the entire surface of the lower surface of the second solid electrolyte layer 6 that defines the ceiling surface of the second internal cavity 40, a bottom electrode portion 51b is formed on substantially the entire surface of the upper surface of the first solid electrolyte layer 4 that defines the bottom surface of the second internal cavity 40, and lateral electrode portions (not shown) connecting the ceiling electrode portion 51a and the bottom electrode portion 51b are formed on the wall surfaces of the spacer layer 5 that define the lateral walls of the second internal cavity 40.

In the sensor element 301 of Variation 2, the residual-oxygen-measuring electrode 44 is formed on substantially the entire surface of the upper surface of the first solid electrolyte layer 4 that defines the bottom surface of the third internal cavity 61.

In the sensor element 301 of Variation 2, adjustment of the oxygen concentration by the main pump cell 21, decomposition of NOx by the target-gas-decomposing pump cell 50, and detection of the residual oxygen by the residual-oxygen-measuring pump cell 41 are respectively conducted in the separate internal cavities that communicate with each other via a diffusion-rate limiting part. It is therefore expected that the oxygen concentration in the measurement-object gas can be adjusted more precisely. As a result, it is expected that the measurement accuracy further improves.

[Variation 3 of Present Invention]

Figure 5:
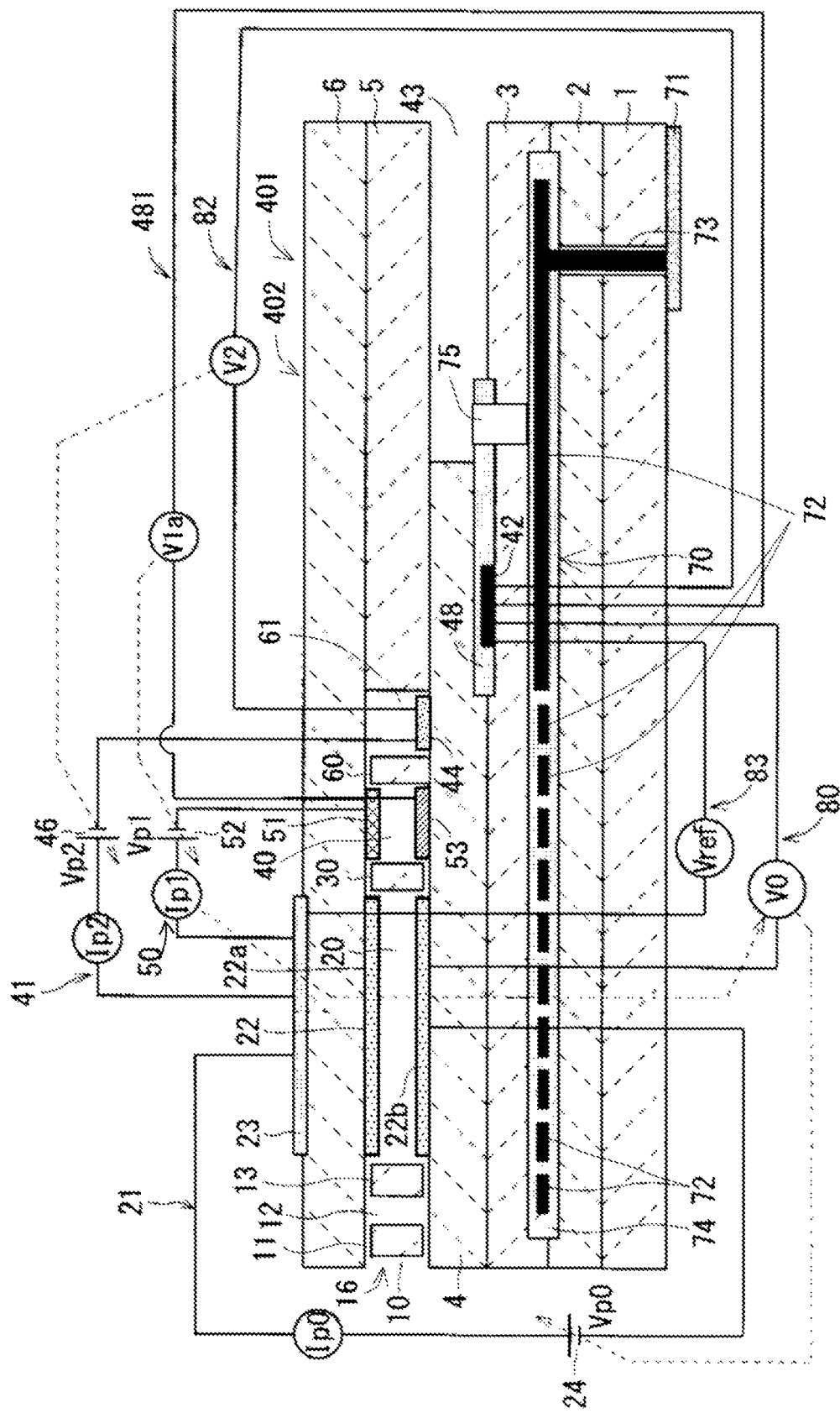
FIG. 5 is a vertical sectional schematic view in the longitudinal direction of a sensor element 401, showing another example of a gas sensor 100.

FIG. 5 is a vertical sectional schematic view of a sensor element 401 of Variation 3 in the longitudinal direction of the sensor element 401. The sensor element 401 of Variation 3 is an embodiment in which adjustment of the oxygen concentration by the main pump cell 21, decomposition of NOx by the target-gas-decomposing pump cell 50, and detection of the residual oxygen by the residual-oxygen-measuring pump cell 41 are respectively conducted in the separate internal cavities that communicate with each other via a diffusion-rate limiting part, as with the sensor element 301 of Variation 2. In FIG. 5, the same member as in FIG. 4 is denoted by the same sign, and description of the same member is omitted.

In the sensor element 401 of Variation 3, the target-gas-decomposing pump electrode 51, and an oxygen-sensing electrode 53 are disposed at positions farther from the front end part in the longitudinal direction of a base part 402 (sensor element 401) than the inner main pump electrode 22 on the inner surface of the measurement-object gas flow part 16. The sensor element 401 of Variation 3 includes an oxygen-partial-pressure sensing cell including the oxygen-sensing electrode 53 and the reference electrode 42 (an oxygen-partial-pressure detection sensor cell 481 for target-gas-decomposing pump control in the sensor element 401 of Variation 3) for detecting the oxygen concentration in the vicinity of the target-gas-decomposing pump electrode 51.

In the sensor element 401 of Variation 3, the target-gas-decomposing pump electrode 51 is formed on substantially the entire surface of the lower surface of the second solid electrolyte layer 6 that defines a ceiling surface of the second internal cavity 40.

In the sensor element 401 of Variation 3, the oxygen-partial-pressure detection sensor cell 481 for target-gas-decomposing pump control is constituted as an electrochemical sensor cell of the oxygen-sensing electrode 53, the reference electrode 42, the first solid electrolyte layer 4, and the third substrate layer 3.

The oxygen-sensing electrode 53 is formed on substantially the entire surface of the upper surface of the first solid electrolyte layer 4 that defines the bottom surface of the second internal cavity 40. The oxygen-sensing electrode 53 is formed as an electrode separate from the target-gas-decomposing pump electrode 51. That is, lateral electrode portions as in the sensor element 301 of Variation 2 does not exist between the target-gas-decomposing pump electrode 51 and the oxygen-sensing electrode 53.

The oxygen-sensing electrode 53 is configured as an electrode for detecting the oxygen concentration in the second internal cavity 40. Likewise the inner main pump electrode 22, the oxygen-sensing electrode 53 may be configured to decompose only oxygen without reducing or decomposing the target gas to be measured (for example, NOx) in the measurement-object gas. Alternatively, likewise the target-gas-decomposing pump electrode 51, the oxygen-sensing electrode 53 may have catalytic activity of reducing (decomposing) a measurement-object gas component (NOx component or the like) in the measurement-object gas. When the oxygen-sensing electrode 53 decomposes NOx, the oxygen generated by decomposition is pumped out by the target-gas-decomposing pump cell 50.

In FIG. 5, the target-gas-decomposing pump electrode 51 is formed on the ceiling surface of the second internal cavity 40, and the oxygen-sensing electrode 53 is formed on the bottom surface of the second internal cavity 40, however, not limited to this configuration. Thus, the oxygen-sensing electrode 53 only has to be provided in the vicinity of the target-gas-decomposing pump electrode 51 so that the oxygen-sensing electrode 53 is exposed to substantially the same atmosphere with the target-gas-decomposing pump electrode 51. For example, the target-gas-decomposing pump electrode 51 may be formed on the bottom surface of the second internal cavity 40, and the oxygen-sensing electrode 53 may be formed on the ceiling surface of the second internal cavity 40. Alternatively, the target-gas-decomposing pump electrode 51 and the oxygen-sensing electrode 53 may be formed on the ceiling surface or the bottom surface of the second internal cavity 40 in parallel with each other in the longitudinal direction of the sensor element 101. The target-gas-decomposing pump electrode 51 and the oxygen-sensing electrode 53 may be formed on the ceiling surface or the bottom surface of the second internal cavity 40 in this order in the longitudinal direction from the front end side of the sensor element 101.

An electromotive force Via detected in the oxygen-partial-pressure detection sensor cell 481 for target-gas-decomposing pump control indicates the oxygen partial pressure in the second internal cavity 40. That is, the electromotive force Via indicates the oxygen partial pressure in the second internal cavity 40 in the condition that the oxygen partial pressure is controlled by the target-gas-decomposing pump cell 50.

Referring to FIG. 4, in the sensor element 301, the oxygen-partial-pressure detection sensor cell 81 for target-gas-decomposing pump control detects the electromotive force V1 between the target-gas-decomposing pump electrode 51 and the reference electrode 42. In the target-gas-decomposing pump cell 50 including the target-gas-decomposing pump electrode 51, the pump current Ip1 flows. The sensor element 101 shown in FIG. 1 also has the same configuration.

According to the consideration of the present inventors, in such a case, it is assumed that the electromotive force V1 between the target-gas-decomposing pump electrode 51 and the reference electrode 42 includes:

(1) a concentration difference electromotive force V(oxygen) generated by oxygen concentration difference between the target-gas-decomposing pump electrode 51 and the reference electrode 42, (2) a thermal electromotive force V(thermal) generated by temperature difference between the target-gas-decomposing pump electrode 51 and the reference electrode 42, and (3) a potential difference generated by flow of the pump current Ip1 through the target-gas-decomposing pump electrode 51, namely, a potential difference V(IR) generated by the pump current Ip1 and a resistance of the target-gas-decomposing pump electrode 51. For example, when oxygen is pumped into the reference electrode 42 to control the reference gas atmosphere in the vicinity of the reference electrode 42, a current also flows through the reference electrode 42. In this case, it is assumed that the electromotive force V1 further includes a potential difference V(IR)' generated by a current flowing through the reference electrode 42 and a resistance of the reference electrode 42, in addition to the above.

Meanwhile, referring to FIG. 5, in the sensor element 401 of Variation 3, the electromotive force Via in the oxygen-partial-pressure detection sensor cell 481 for target-gas-decomposing pump control is detected as an electromotive force between the oxygen-sensing electrode 53 that is separate from the target-gas-decomposing pump electrode 51, and the reference electrode 42. Since a current does not flow through the oxygen-sensing electrode 53, the electromotive force Via does not include a potential difference corresponding to the aforementioned (3) potential difference V(IR). That is, the value of the pump current Ip1 flowing through the target-gas-decomposing pump cell 50 does not affect the electromotive force Via. For example, even when the pump current Ip1 is increased (set value $Ip1_{SET}$ is set at a large value) at the time of measuring a high concentration of the target gas to be measured, the electromotive force Via is not affected. Therefore, the electromotive force Via allows more precise detection of the oxygen partial pressure in the second internal cavity 40. Thus, it is possible to control the oxygen partial pressure in the second internal cavity 40, namely, the residual oxygen concentration in the measurement-object gas that reaches the residual-oxygen-measuring electrode 44 more precisely. As a result, it is possible to measure the NOx concentration more accurately. In particular, even when a high concentration of the target gas to be measured is measured, high measurement accuracy can be maintained.

[Comparative Form]

Figure 6:
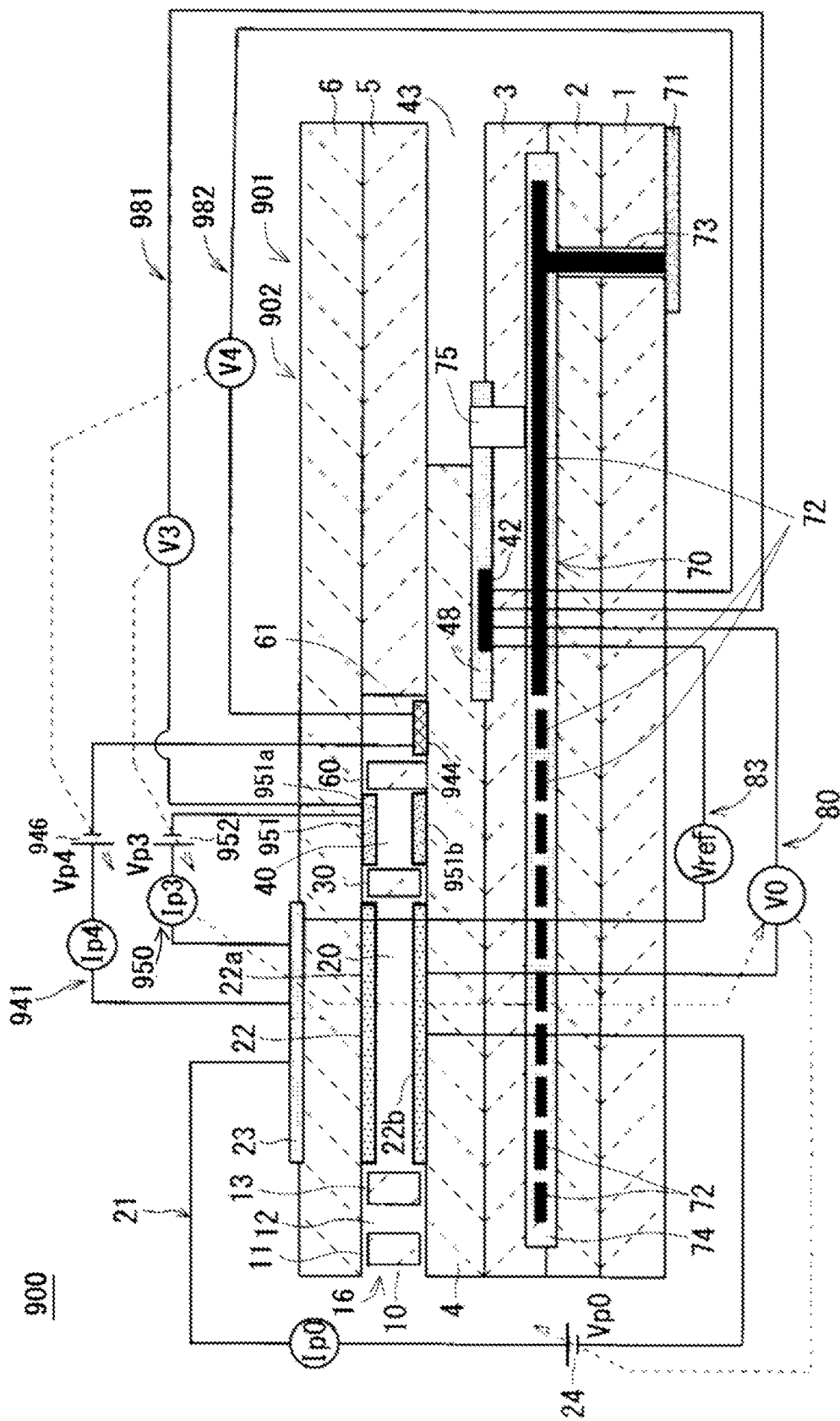
FIG. 6 is a vertical sectional schematic view in the longitudinal direction of a sensor element 901, showing one example of a general configuration of a gas sensor 900 of Comparative form.

FIG. 6 is a vertical sectional schematic view in the longitudinal direction of a sensor element 901, showing one example of a general configuration of a gas sensor 900 of Comparative form. The internal cavities 20, 40, 61 of the measurement-object gas flow part 16 are arranged in the same manner as those in the sensor element 301 of Variation 2. In FIG. 6, the same member as in FIG. 4 is denoted by the same sign, and description of the same member is omitted.

The sensor element 901 of Comparative form includes the main pump cell 21 for adjusting an oxygen concentration in a measurement-object gas, an auxiliary pump cell 950 for further adjusting the oxygen concentration, and a measurement pump cell 941 for detecting a target gas to be measured.

The auxiliary pump cell 950 is an auxiliary electrochemical pump cell composed of an auxiliary pump electrode 951 having a ceiling electrode portion 951a disposed on substantially the entire surface of the lower surface of the second solid electrolyte layer 6 facing with the second internal cavity 40, the outer pump electrode 23, and the second solid electrolyte layer 6. The auxiliary pump cell 950 is configured to pump out oxygen in the atmosphere in the second internal cavity 40, by applying a desired voltage Vp1 between the auxiliary pump electrode 951 and the outer pump electrode 23 by a variable power supply 952. Also, the auxiliary pump electrode 951, the reference electrode 42, the second solid electrolyte layer 6, the spacer layer 5, the first solid electrolyte layer 4, and the third substrate layer 3 constitute an oxygen-partial-pressure detection sensor cell 81 for auxiliary pump control.

The auxiliary pump electrode 51 is also configured to decompose only oxygen without reducing (decomposing) NOx as with the case of the inner main pump electrode 22. The auxiliary pump electrode 951 has the tunnel-like structure, where the ceiling electrode portion 951a is formed on the second solid electrolyte layer 6 that defines the ceiling surface of the second internal cavity 40, a bottom electrode portion 951b is formed on the first solid electrolyte layer 4 that defines the bottom surface of the second internal cavity 40, and lateral electrode portions (not shown) connecting the ceiling electrode portion 951a and the bottom electrode portion 951b are formed on the wall surfaces of the spacer layer 5 that define the lateral walls of the second internal cavity 40.

The measurement pump cell 941 is an electrochemical pump cell composed of a measurement electrode 944 disposed on the upper surface of the first solid electrolyte layer 4 facing with the third internal cavity 61, the outer pump electrode 23, the second solid electrolyte layer 6, the spacer layer 5, and the first solid electrolyte layer 4. Also, the measurement electrode 944, the reference electrode 42, the second solid electrolyte layer 6, the spacer layer 5, the first solid electrolyte layer 4, the third substrate layer 3 constitute an oxygen-partial-pressure detection sensor cell 982 for measurement pump control.

The measurement electrode 944 functions also as a NOx reduction catalyst that reduces NOx present in the atmosphere in the third internal cavity 61. The measurement electrode 944 is formed on substantially the entire surface of the upper surface of the first solid electrolyte layer 4 that defines the bottom surface of the third internal cavity 61.

In the gas sensor 900 of Comparative form, the pump current Ip0 is controlled by performing feedback control of the pump voltage Vp0 so that the electromotive force V0 in the oxygen-partial-pressure detection sensor cell 80 for main pump control is constant. Thus, the oxygen concentration in the vicinity of the inner main pump electrode 22 in the first internal cavity 20 can be maintained at a predetermined constant value. The pump current Ip0 in the main pump cell 21 varies depending on the oxygen concentration in the measurement-object gas.

The pump voltage Vp3 of the variable power supply 952 in the auxiliary pump cell 950 is feedback controlled so that the electromotive force V3 in the oxygen-partial-pressure detection sensor cell 981 for auxiliary pump control is a predetermined value. Thus, the oxygen partial pressure in the atmosphere in the second internal cavity 40 is controlled to such a low partial pressure that does not substantially affect measurement of NOx. In addition, a set value of the electromotive force V0 in the oxygen-partial-pressure detection sensor cell 80 for main pump control is set on the basis of a pump current Ip3 in the auxiliary pump cell 950 so that the pump current Ip3 is a constant value.

The measurement-object gas introduced into the second internal cavity 40 reaches the measurement electrode 44 in the third internal cavity 61 through the fourth diffusion-rate limiting part 60 under the condition that the oxygen partial pressure is controlled. Nitrogen oxide in the measurement-object gas around the measurement electrode 944 is reduced ($2NO \rightarrow N_2 + O_2$) to generate oxygen. The generated oxygen is to be pumped by the measurement pump cell 941, and at this time, a voltage Vp4 of the variable power supply 946 is controlled so that the electromotive force V4 detected by the oxygen-partial-pressure detection sensor cell 982 for measurement pump control is constant. Since the amount of oxygen generated around the measurement electrode 944 is proportional to the concentration of nitrogen oxide in the measurement-object gas, nitrogen oxide concentration in the measurement-object gas is calculated by using the pump current Ip4 in the measurement pump cell 941.

EXAMPLES

Hereinafter, the case of actually manufacturing a sensor element and conducting a test is described as Examples. The present invention is not limited to the following Examples.

Examples 1

As Examples 1, the sensor element 101 shown in FIG. 1 and FIG. 2 was manufactured.

An electrode paste to be used for each of the electrodes 22, 51, 44 was prepared in the following manner. Each electrode paste was prepared by adding a solvent, a binder, and a dispersing agent to mixed powder of a metal component and a ceramic component mixed in a weight ratio of metal component:ceramic component=6.0:4.0. As a ceramic component of each electrode paste, $ZrO_2$ was used in any electrode paste. The metal component of each electrode paste was as follows.

In the electrode paste to be used for the inner main pump electrode 22, Pt and Au were used as the metal component. The concentration of Au to the total amount of Pt and Au was 0.80% by weight. In the electrode paste to be used for the target-gas-decomposing pump electrode 51, Pt and Rh were used as the metal component. The concentration of Rh to the total amount of Pt and Rh was 50% by weight. In the electrode paste to be used for the residual-oxygen-measuring electrode 44, Pt and Au were used as the metal component as with the case of the electrode paste to be used for the inner main pump electrode 22. The concentration of Au to the total amount of Pt and Au was 0.80% by weight.

The sensor element 101 was manufactured using prepared electrode pastes according to the aforementioned production method of the sensor element 101. A gas sensor 100 in which the manufactured sensor element 101 was incorporated was manufactured to conduct the later-described durability test.

Examples 2

As Examples 2, the sensor element 201 shown in FIG. 3 was manufactured.

Each electrode paste prepared in Example 1 was used. Each electrode paste was printed on the second solid electrolyte layer 6 so that the target-gas-decomposing pump electrode 51 and the residual-oxygen-measuring electrode 44 were arranged in parallel. Except for the above, the sensor element 201 was prepared in the same manner as for the sensor element 101 of Example 1. A gas sensor in which the manufactured sensor element 201 was incorporated was manufactured to conduct the later-described durability test.

Examples 3

As Examples 3, the sensor element 301 shown in FIG. 4 was manufactured.

In the blank sheet to be used for the spacer layer 5, penetrating parts such as internal cavities 20, 40, 61 shown in FIG. 4 was formed. Each electrode paste prepared in Example 1 was used. The electrode paste to be used for the inner main pump electrode 22 was printed at predetermined positions of the second solid electrolyte layer 6, the first solid electrolyte layer 4, and the spacer layer 5. The electrode paste to be used for the target-gas-decomposing pump electrode 51 was printed at predetermined positions of the second solid electrolyte layer 6, the first solid electrolyte layer 4, and the spacer layer 5. The electrode paste to be used for the residual-oxygen-measuring electrode 44 was printed at a predetermined position of the first solid electrolyte layer 4. Except for the above, the sensor element 301 was prepared in the same manner as for the sensor element 101 of Example 1. A gas sensor in which the manufactured sensor element 301 was incorporated was manufactured to conduct the later-described durability test.

Examples 4

As Examples 4, the sensor element 401 shown in FIG. 5 was manufactured.

Each electrode paste prepared in Example 1 was used. The electrode paste to be used for the oxygen-sensing electrode 53 was prepared in the same manner as for the electrode pastes prepared in Example 1 except that Pt was used as the metal component. The electrode paste to be used for the target-gas-decomposing pump electrode 51 was printed at a predetermined position of the second solid electrolyte layer 6. The electrode paste to be used for the oxygen-sensing electrode 53 was printed at a predetermined position of the first solid electrolyte layer 4. Except for the above, the sensor element 401 was prepared in the same manner as for the sensor element 301 of Example 3. A gas sensor in which the manufactured sensor element 401 was incorporated was manufactured to conduct the later-described durability test.

Comparative Example 1

As Comparative Example, the sensor element 901 shown in FIG. 6 was manufactured.

As the electrode paste to be used for the auxiliary pump electrode 951, the same electrode paste as for the inner main pump electrode 22 was used. As the electrode paste to be used for the measurement electrode 944, the same electrode paste as for the target-gas-decomposing pump electrode 51 was used. Except for the above, the sensor element 900 was prepared in the same manner as for the sensor element 301 of Example 3. A gas sensor 900 in which the manufactured sensor element 901 was incorporated was manufactured to conduct the later-described durability test.

[Durability Test]

A durability test using a diesel engine was conducted, and the degree of deterioration in NOx detection sensitivity was evaluated. Before and after the durability test, NOx sensitivity (Ip2 current value) of the gas sensor at a NO concentration of 500 ppm was measured, and a rate of change in NOx sensitivity before and after the durability test was calculated. The degree of deterioration in NOx detection sensitivity was evaluated and judged according to the rate of change in NOx sensitivity. Specifically, the test was conducted in the following manner.

Measurement of the NOx sensitivity and the durability test were conducted while the gas sensor was driven. The gas sensors of Examples 1 to 4 and Comparative Example 1 were driven respectively with the set values shown in Table 1.

TABLE 1

|  | Set value $V1_{SET}$ | Set value $Ip1_{SET}$ | Set value $V2_{SET}$ |
|---|---|---|---|
| Example 1 | 385 mV | 7 μA | 400 mV |
| Example 2 | 385 mV | 7 μA | 400 mV |
| Example 3 | 385 mV | 7 μA | 400 mV |
|  | Set value $V1a_{SET}$ | Set value $Ip1_{SET}$ | Set value $V2_{SET}$ |
| Example 4 | 385 mV | 7 μA | 400 mV |
|  | Set value $V3_{SET}$ | Set value $Ip3_{SET}$ | Set value $V4_{SET}$ |
| Comparative Example 1 | 385 mV | 7 μA | 400 mV |

First, the gas sensor of Example 1 was measured in a model gas device. The gas sensor of Example 1 was attached to a piping for measurement of the model gas device. The gas sensor of Example 1 was driven. A model gas satisfying NO=500 ppm and $O_2$=0% was flowed in the piping for measurement, and Ip2 current value ($Ip2_{fresh}$) of the gas sensor in Example 1 was measured. For each of Examples 2 to 4 and Comparative Example 1, Ip2 current value ($Ip2_{fresh}$) was measured in the same manner. The gas components other than NO and $O_2$ in the model gas used for measurement were $H_2O$ (3%) and $N_2$ (remainder).

Next, a durability test using a diesel engine was conducted. The gas sensor of each of Examples 1 to 4 and Comparative Example 1 was attached to a piping of an exhaust gas pipe of an automobile. Then, the gas sensor of each of Examples 1 to 4 and Comparative Example 1 was driven. In this condition, an operation pattern of 40 minutes at an engine speed ranging from 1500 to 3500 rpm, and a load torque ranging from 0 to 350 N·m was repeated until 4000 hours had lapsed. In the operation pattern, the gas temperature was 200° C. to 600° C., and the NOx concentration was 0 to 1500 ppm.

At the point of time after a lapse of 500 hours from the start of the test, the durability test was suspended, and the gas sensors of Examples 1 to 4 and Comparative Example 1 were taken out. For the taken out gas sensors of Examples 1 to 4 and Comparative Example 1, Ip2 current value ($Ip2_{aged500H}$) of each gas sensor in the gas sensor after a lapse of 500 hours of the durability test was measured in the method described above.

For each of the gas sensors of Examples 1 to 4 and Comparative Example 1, the amount of change in the NOx detection sensitivity before and after the durability test was calculated. In other words, a rate of change (rate of change in NOx sensitivity) of the Ip2 current value ($Ip2_{aged500H}$) after a lapse of 500 hours of the durability test to the Ip2 current value ($Ip2_{fresh}$) before the durability test was calculated.

Rate of change in NOx sensitivity (%)=($Ip2_{aged500H}$/$Ip2_{fresh}$−1)×100

After measuring the Ip2 current value ($Ip2_{aged500H}$) after a lapse of 500 hours of the durability test, the gas sensors of Examples 1 to 4 and Comparative Example 1 were attached again to the piping of the exhaust gas pipe. Then, the aforementioned durability test using a diesel engine was resumed, and the durability test was continued until the cumulative lapse time had reached 1000 hours.

For each of the gas sensors of Examples 1 to 4 and Comparative Example 1 after a lapse of 1000 hours of the durability test, a rate of change (rate of change in NOx sensitivity) of the Ip2 current value ($Ip2_{aged1000H}$) after a lapse of 1000 hours of the durability test to the Ip2 current value ($Ip2_{fresh}$) before the durability test was calculated in the same manner as the case after the lapse of 500 hours.

Figure 7:
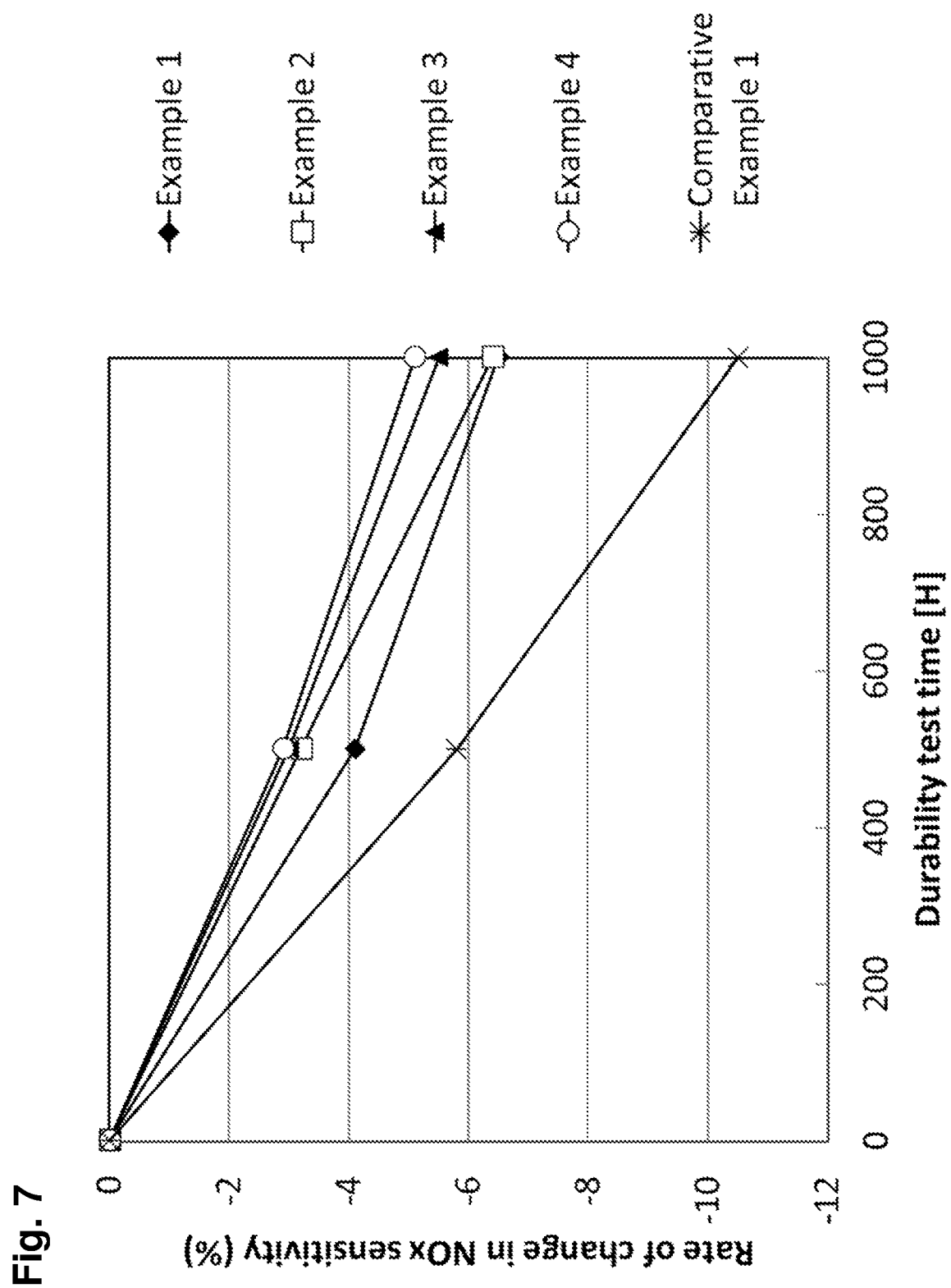
FIG. 7 is a graph showing durability test results of Examples 1 to 4 and Comparative Example 1. The vertical axis of the graph represents the rate of change in NOx sensitivity (%) and the horizontal axis represents the durability time (hours; H).

Table 2 and FIG. 7 shows the durability test results of Examples 1 to 4 and Comparative Example 1. In FIG. 7, the vertical axis of the graph represents the rate of change in NOx sensitivity (%) and the horizontal axis represents the durability time (hours).

TABLE 2

| | Rate of change in NOx sensitivity (%) | |
|---|---|---|
| | After 500 hours | After 1000 hours |
| Example 1 | −4.1 | −6.5 |
| Example 2 | −3.2 | −6.4 |
| Example 3 | −3.0 | −5.5 |
| Example 4 | −2.9 | −5.1 |
| Comparative Example 1 | −5.8 | −10.5 |

As shown in Table 2 and FIG. 7, it was confirmed that the rate of change in NOx sensitivity (%) can be suppressed in any gas sensor of Examples 1 to 4 in comparison with the gas sensor 900 of Comparative example 1.

As described above, according to the present invention, it is possible to obtain the concentration of the target gas to be measured by removing a part of oxygen derived from the target gas to be measured in the target-gas-decomposing pump cell 50, and detecting the residual oxygen of the concentration corresponding to the concentration of the target gas to be measured as a current value in the residual-oxygen-measuring pump cell 41.

According to the present invention, even when Au in the inner main pump electrode 22 evaporates and the evaporated Au adheres to the residual-oxygen-measuring electrode 44 as a result of using the gas sensor for a long time under high oxygen concentration at a high temperature range, the catalytic activity for oxygen of the residual-oxygen-measuring electrode 44 is maintained, and thus the detection accuracy of the gas sensor does not deteriorate. Therefore, it is possible to suppress deterioration in detection accuracy of the gas sensor due to use.

Thus, deterioration in detection accuracy of the gas sensor due to use of the gas sensor can be suppressed. In other words, according to the present invention, it is possible to suppress the change with time of the detected value of the target gas to be measured. As a result, the durability of the gas sensor improves.

Also, according to the present invention, the target gas to be measured is not directly detected. Instead, the target gas to be measured is decomposed and a certain amount of the total oxygen in the measurement-object gas including the oxygen generated by decomposition is removed in the target-gas-decomposing pump cell 50, and then residual oxygen in the measurement-object gas is detected in the residual-oxygen-measuring pump cell 41. The amount of oxygen removed in the target-gas-decomposing pump cell 50 is correlated with the value of pump current Ip1 flowing through the target-gas-decomposing pump cell 50. Therefore, by the value of the pump current Ip1 in the target-gas-decomposing pump cell 50, it is possible to adjust the range of the residual oxygen concentration reaching the residual-oxygen-measuring electrode 44. As a result, the gas sensor can be adapted even when the concentration of the target gas to be measured in the measurement-object gas largely varies. Thus, according to the present invention, it is possible to accurately measure the measurement-object gas including a wide concentration range of the target gas to be measured.

Further, the present invention includes the following embodiment.

A gas sensor for detecting a target gas to be measured in a measurement-object gas, the gas sensor comprising:
  a base part in an elongated plate shape, including a plurality of oxygen-ion-conductive solid electrolyte layers stacked;
  a measurement-object gas flow part for introduction and flow of a measurement-object gas through one end part in a longitudinal direction of the base part;
  a main pump cell including an inner main pump electrode disposed on an inner surface of the measurement-object gas flow part, and an outer pump electrode disposed at a position different from the measurement-object gas flow part on the base part and corresponding to the inner main pump electrode;
  a target-gas-decomposing pump cell including a target-gas-decomposing pump electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the target-gas-decomposing pump electrode;
  a residual-oxygen-measuring pump cell including a residual-oxygen-measuring electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the residual-oxygen-measuring electrode; and a reference electrode disposed inside the base part to be in contact with a reference gas, wherein the target-gas-decomposing pump electrode comprises a metal material that has catalytic activity of decomposing a target gas to be measured;

the main pump cell has a function to adjust an oxygen concentration in a measurement-object gas introduced into the measurement-object gas flow part to a predetermined concentration, to obtain the measurement-object gas in which the oxygen concentration is adjusted to the predetermined concentration;

the target-gas-decomposing pump cell has a function to decompose a target gas to be measured in the measurement-object gas on the target-gas-decomposing pump electrode, and pumping out a predetermined constant amount of a total oxygen including an oxygen generated by decomposing the target gas to be measured in the measurement-object gas so as to maintain a current value flowing through the target-gas-decomposing pump cell constant at a predetermined set value; and the residual-oxygen-measuring pump cell has a function to obtain a detected current value that corresponds to a residual oxygen existed in the measurement-object gas flow part.

What is claimed is:

1. A sensor element for detecting a target gas to be measured in a measurement-object gas, the sensor element comprising:
    a base part in an elongated plate shape, including a plurality of oxygen-ion-conductive solid electrolyte layers stacked;
    a measurement-object gas flow part for introduction and flow of the measurement-object gas through one end part in a longitudinal direction of the base part;
    a main pump cell including an inner main pump electrode disposed on an inner surface of the measurement-object gas flow part, and an outer pump electrode disposed at a position different from the measurement-object gas flow part on the base part and corresponding to the inner main pump electrode;
    a target-gas-decomposing pump cell including a target-gas-decomposing pump electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the target-gas-decomposing pump electrode;
    a residual-oxygen-measuring pump cell including a residual-oxygen-measuring electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the residual-oxygen-measuring electrode; and
    a reference electrode disposed inside the base part to be in contact with a reference gas,
    wherein the target-gas-decomposing pump electrode comprises a metal material that has catalytic activity of decomposing the target gas to be measured, and the residual-oxygen-measuring electrode comprises a metal material that does not have catalytic activity of decomposing the target gas to be measured.

2. The sensor element according to claim 1, wherein the target-gas-decomposing pump electrode and the residual-oxygen-measuring electrode are disposed in this order in series in the longitudinal direction of the base part at positions farther from the one end part in the longitudinal direction of the base part than the inner main pump electrode on the inner surface of the measurement-object gas flow part.

3. The sensor element according to claim 1, wherein the target-gas-decomposing pump electrode and the residual-oxygen-measuring electrode are disposed in parallel in the longitudinal direction of the base part at positions farther from the one end part in the longitudinal direction of the base part than the inner main pump electrode on the inner surface of the measurement-object gas flow part.

4. The sensor element according to claim 1, wherein the target-gas-decomposing pump electrode and a further oxygen-sensing electrode are disposed at positions farther from the one end part in the longitudinal direction of the base part than the inner main pump electrode on the inner surface of the measurement-object gas flow part, and
    the sensor element further comprises an oxygen-partial-pressure-sensing cell including the oxygen-sensing electrode and the reference electrode.

5. The sensor element according to claim 1, wherein the target gas to be measured is NOx.

6. The sensor element according to claim 1, wherein the metal material included in the target-gas-decomposing pump electrode includes at least one selected from the group consisting of platinum and rhodium as a metal that has catalytic activity of decomposing the target gas to be measured.

7. The sensor element according to claim 1, wherein the metal material included in the target-gas-decomposing pump electrode does not include gold, or includes gold to the extent that catalytic activity of decomposing the target gas to be measured is not inhibited.

8. The sensor element according to claim 1, wherein the metal material included in the residual-oxygen-measuring electrode includes platinum, and includes at least one selected from the group consisting of gold and silver as a metal that reduces catalytic activity of decomposing the target gas to be measured.

9. The sensor element according to claim 1, wherein the metal material included in the residual-oxygen-measuring electrode includes gold, and
    a content of the gold is 0.3% by weight or more in the metal material included in the residual-oxygen-measuring electrode.

10. The sensor element according to claim 1, wherein at least two selected from the group consisting of the outer pump electrode corresponding to the inner main pump electrode, the outer pump electrode corresponding to the target-gas-decomposing pump electrode, and the outer pump electrode corresponding to the residual-oxygen-measuring electrode, are formed as an integrated electrode.

11. A detection method of a target gas to be measured in a measurement-object gas using a sensor element, the sensor element comprising:
    a base part in an elongated plate shape, including a plurality of oxygen-ion-conductive solid electrolyte layers stacked;

a measurement-object gas flow part for introduction and flow of the measurement-object gas through one end part in a longitudinal direction of the base part;

a main pump cell including an inner main pump electrode disposed on an inner surface of the measurement-object gas flow part, and an outer pump electrode disposed at a position different from the measurement-object gas flow part on the base part and corresponding to the inner main pump electrode;

a target-gas-decomposing pump cell including a target-gas-decomposing pump electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the target-gas-decomposing pump electrode;

a residual-oxygen-measuring pump cell including a residual-oxygen-measuring electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the residual-oxygen-measuring electrode; and a reference electrode disposed inside the base part to be in contact with a reference gas, wherein the target-gas-decomposing pump electrode comprises a metal material that has catalytic activity of decomposing a target gas to be measured, and the residual-oxygen-measuring electrode comprises a metal material that does not have catalytic activity of decomposing the target gas to be measured, the detection method comprising:

an oxygen-concentration-adjusting step of adjusting an oxygen concentration in the measurement-object gas introduced into the measurement-object gas flow part to a predetermined concentration by the main pump cell, to obtain the measurement-object gas in which the oxygen concentration is adjusted to the predetermined concentration;

a current-value-controlling step of decomposing the target gas to be measured in the measurement-object gas on the target-gas-decomposing pump electrode by the target-gas-decomposing pump cell, and pumping out a predetermined constant amount of a total oxygen including an oxygen generated by decomposing the target gas to be measured in the measurement-object gas by the target-gas-decomposing pump cell so as to maintain a current value flowing through the target-gas-decomposing pump cell constant at a predetermined set value;

a detecting step of obtaining a detected current value that corresponds to a residual oxygen existed in the measurement-object gas flow part, by the residual-oxygen-measuring pump cell; and a concentration-calculating step of calculating a concentration of the target gas to be measured based on the detected current value.

12. The detection method according to claim 11, wherein, in the current-value-controlling step, the set value of the current value is determined by a total amount of the measurement-object gas that reaches the target-gas-decomposing pump electrode in the sensor element.

13. The detection method according to claim 11, wherein the set value of the current value in the current-value-controlling step is set as a plurality of set values, and the current value-controlling step further comprises a set-value-determining step of determining any set value to be used of the plurality of set values.

14. The detection method according to claim 13, wherein, in the set-value-determining step, the any set value to be used of the plurality of set values is determined based on a predicted concentration of the target gas to be measured in the measurement-object gas.

* * * * *